United States Patent
Kim et al.

(10) Patent No.: US 11,241,501 B2
(45) Date of Patent: Feb. 8, 2022

(54) ANTICANCER PRODRUG FOR OVERCOMING DRUG RESISTANCE

(71) Applicant: Korea University Research and Business Foundation, Seoul (KR)

(72) Inventors: Jong Seung Kim, Seongnam-si (KR); Amit Sharma, Seoul (KR); Min Goo Lee, Seoul (KR); Miae Won, Seoul (KR); Jin Yong Lee, Suwon-si (KR); Sung-Gil Chi, Goyang-si (KR); Jonathan L. Sessler, Austin, TX (US)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 16/547,726

(22) Filed: Aug. 22, 2019

(65) Prior Publication Data
US 2020/0129626 A1   Apr. 30, 2020

(30) Foreign Application Priority Data
Oct. 24, 2018 (KR) .................. 10-2018-0127337

(51) Int. Cl.
*A61K 47/55* (2017.01)
*A61K 31/704* (2006.01)

(52) U.S. Cl.
CPC ............ *A61K 47/55* (2017.08); *A61K 31/704* (2013.01)

(58) Field of Classification Search
CPC ..... A61K 47/55; A61K 31/704; A61K 31/519
See application file for complete search history.

(56) References Cited

FOREIGN PATENT DOCUMENTS

| KR | 10-1465626 B1 | 12/2014 | |
|---|---|---|---|
| KR | 10-2017-0083998 A | 7/2017 | |
| WO | WO 2012/167255 A1 | 12/2012 | |
| WO | WO 2012167255 | * 12/2012 | ............ A61K 31/56 |

OTHER PUBLICATIONS

Lee, Min Hee et al., "Fluorogenic reaction-based prodrug conjugates as targeted cancer theranostics", *Royal Society of Chemistry*, vol. 47, No. 1, Jan. 7, 2018 (pp. 1-26).

Sharma et al., "Overcoming Drug Resistance by Targeting Cancer Bioenergetics with an Activatable Prodrug," CellPress, Oct. 11, 2018, 4 (10), pp. 2370-2383.

Sharma et al., "Targeting cancer bioenergetics combined with prodrug activation overcomes drug resistance," The $2^{nd}$ Asian Conference on Chemosensors & Imaging Probes, Oct. 23-26, 2017, Beijing, China, 10 pages.

* cited by examiner

*Primary Examiner* — Pancham Bakshi
(74) *Attorney, Agent, or Firm* — NSIP Law

(57) ABSTRACT

Disclosed is an anticancer prodrug that disturbs energy metabolism in cancer cells to overcome drug resistance. The anticancer prodrug has a structure including a pyruvate dehydrogenase kinase (PDK) inhibitor moiety, a mitochondrial targeting group, and an anthracycline moiety reversibly connected to the PDK inhibitor moiety and the targeting group.

4 Claims, 57 Drawing Sheets

NCI/Dox

| C1 | C2 |
|---|---|
|  |  |
|  |  |

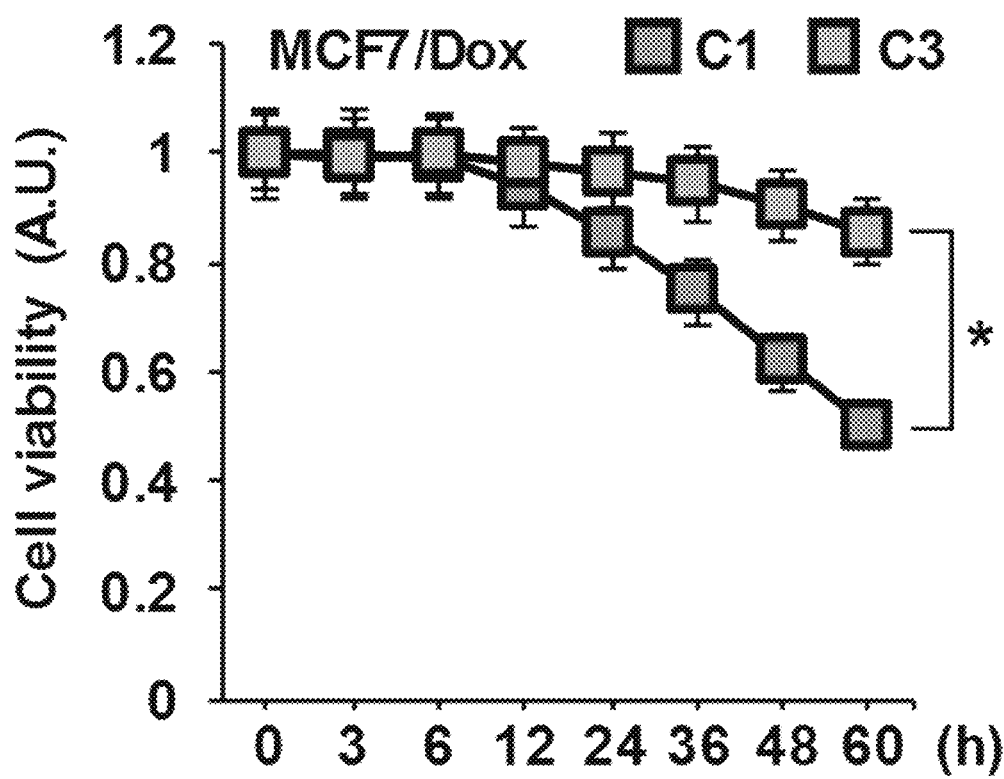

ANTICANCER PRODRUG FOR OVERCOMING DRUG RESISTANCE

CROSS-REFERENCE TO RELATED APPLICATION(S)

This application claims the benefit under 35 USC § 119(a) of Korean Patent Application No. 10-2018-0127337 filed on Oct. 24, 2018, in the Korean Intellectual Property Office, the entire disclosure of which is incorporated herein by reference for all purposes.

BACKGROUND OF THE INVENTION

1. Field of the Invention

The present invention relates to an anticancer prodrug that disturbs energy metabolism in cancer cells to overcome drug resistance.

2. Description of the Related Art

Cancer chemotherapeutics play a critical role in the management of malignant disease. Unfortunately, drug resistance often presents a barrier to successful clinical outcomes. Drug resistance is associated with lethal side effects and increased recurrence rates. Initially, many tumors are responsive to chemotherapy; however, over time, they become resistant owing to the rapid proliferation of small subpopulations of resistant cells that survive during the initial treatment periods. These problems are exacerbated when acquired resistance from one drug is transferred to other anticancer treatment regimens despite mechanistic and structural differences in the agents being used. This latter phenomenon is generally referred to as multidrug resistance (MDR). Although other factors can contribute, it is estimated that innate or induced drug resistance poses a serious risk in approximately 90% of metastatic cancer patients and is correlated with most treatment failures. Typically, an increase in drug efflux mediated by ATP-binding cassette (ABC) transmembrane proteins, such as ABCG2 and MDR1 (p-glycoprotein), is the primary reason for chemoresistance seen in a variety of cancers. This is true even though these proteins play positive roles in normal physiology. Despite continuous efforts to develop effective modulators of drug transport proteins, fully satisfactory clinical benefits have yet to be realized.

During the early stage of carcinogenesis, aerobic glycolysis (the Warburg effect) usually dominates over oxidative phosphorylation (OXPHOS). This is ascribed to the inherent need to meet the urgent energy demands and metabolic requirements associated with uncontrolled tumor growth. In mammalian cells, pyruvate serves as an intermediary in both processes. Its fate is regulated by pyruvate dehydrogenase (PDH), a mitochondrial gatekeeper enzyme. PDH activity itself is modulated by pyruvate dehydrogenase kinase (PDK). A direct correlation between PDH and PDK in promoting metabolic alterations associated with chemoresistance has been established. In addition, the glycolytic byproducts associated with aerobic metabolism provide advantages to rapid cellular proliferation, including reduced apoptosis, enhanced cell mobility, increased efflux rates, and augmented metastatic potential, although a few positive outcomes in improving chemosensitivity have been noted. Given these correlations, the ability to alter aberrant metabolic adaptations in tumors and restore OXPHOS has appeal in the context of cancer therapy.

So-called targeted drugs hold promise in terms of improving the survival rates and quality of life for cancer patients. In addition, targeted therapeutics may be able to bypass some of the known MDR mechanisms, thereby preventing chemoresistance. To date, a number of localizing agents, including cancer-specific receptor inhibitors, peptides, polymers, ionic liquids, dendrimers, metal organic frameworks, and nanoparticles, have been explored in the context of cancer drug development [Lee, M. H., Sharma, A., Chang, M. J., Lee, J., Son, S., Sessler, J. L., Kang, C., and Kim, J. S. (2018). Fluorogenic reaction-based prodrug conjugates as targeted cancer theranostics. Chem. Soc. Rev. 47, 28-52]. Similar approaches have also been successfully utilized in the diagnosis and treatment of pathogenic bacterial infections, neurologic disorders, inflammation, and immune system diseases.

However, a targeting strategy that also successfully overcomes unfavorable alterations in metabolism has never been reported in the context of cancer drug discovery.

SUMMARY OF THE INVENTION

Based on the above background art, the present invention intends to provide an anticancer prodrug that can induce alterations in tumor-specific energy metabolism in cancer cells to effectively overcome drug resistance.

An aspect of the present invention provides an anticancer prodrug that disturbs energy metabolism in cancer cells to overcome drug resistance.

The anticancer prodrug may have a structure including a pyruvate dehydrogenase kinase (PDK) inhibitor moiety, a mitochondrial targeting group, and an anthracycline moiety reversibly connected to the PDK inhibitor moiety and the targeting group. The structure of the anticancer prodrug will be described in detail below.

The anticancer prodrug of the present invention may be activated by carboxylesterase to release the PDK inhibitor moiety and the anthracycline moiety.

The released PDK inhibitor moiety may shift cancer cell metabolism from aerobic glycolysis (the Warburg effect) to oxidative phosphorylation (OXPHOS).

The anticancer prodrug of the present invention can induce alterations in tumor-specific energy metabolism in cancer cells to effectively inhibit the growth of drug-resistant tumors, achieving improved anticancer effects.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 2 shows chemical activation of compound C1. Specifically.

FIG. 3 shows cell localization and viability assays of compounds C1-C6. Specifically.

FIG. 4 shows C1-induced apoptosis in multidrug-resistant tumor cells. Specifically.

FIG. 5 shows anticancer activity of C1 versus combination of DCA and doxorubicin in vitro and in vivo. Specifically.

FIG. 19B shows the effect of C1 on MCF7/Dox cell viability. Cells were treated with 10 μM of the probes for the indicated times. Cell viability was determined using a WST-1 assay (mean±SD, n=3, * p<0.05).

FIG. 23 shows analysis of the effect of C1, C2, C3, C4, and DMSO in vivo. Specifically.

DETAILED DESCRIPTION OF THE INVENTION

The present invention will now be described in more detail.

The present invention is directed to an anticancer prodrug that can induce alterations in tumor-specific energy metabolism in cancer cells to effectively overcome drug resistance. Specifically, the anticancer prodrug of the present invention has a structure including a pyruvate dehydrogenase kinase (PDK) inhibitor moiety, a mitochondrial targeting group, and an anthracycline moiety reversibly connected to the PDK inhibitor moiety and the targeting group.

According to one embodiment of the present invention, the PDK inhibitor moiety may be represented by Structural Formula 1:

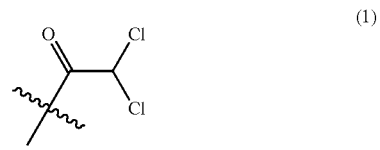

(1)

According to one embodiment of the present invention, the mitochondrial targeting group may be represented by Structural Formula 2:

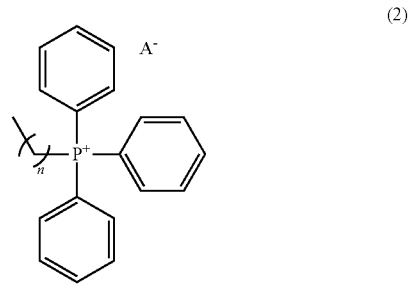

(2)

wherein A' is an anion selected from halogen, hydroxyl, carboxylate, sulfate, sulfamate, sulfonate, phosphate, phosphonate, boronate, and poly(ethyleneoxy) anions and n is an integer from 1 to 30.

According to one embodiment of the present invention, the anthracycline may be selected from doxorubicin, daunorubicin, epirubicin, idarubicin, and mitoxantrone.

The PDK inhibitor moiety, the mitochondrial targeting group, and the anthracycline moiety may be connected to one another through a linker represented by Formula 1 or 2:

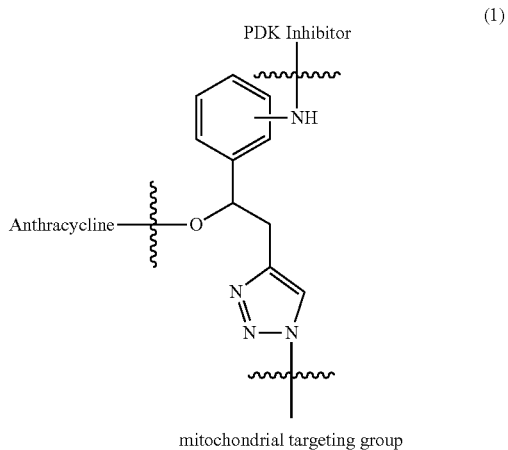

(1)

-continued

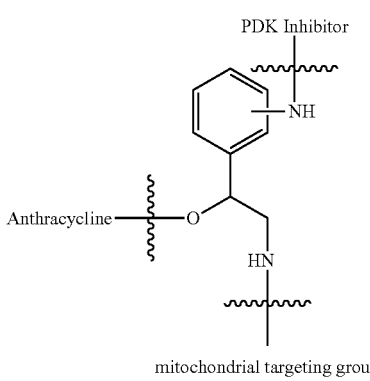

(2)

Specifically, the anticancer prodrug of the present invention includes a doxorubicin (Dox) moiety reversibly connected to a dichloroacetic acid (DCA) subunit as the PDK inhibitor moiety and a triphenylphosphonium (TPP) moiety as the mitochondrial targeting group.

More specifically, the anticancer prodrug of the present invention is the target-specific compound (compound C1) represented by Formula 3:

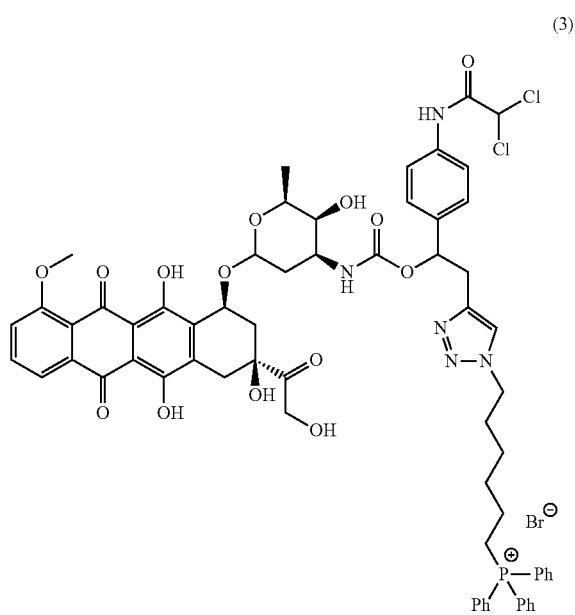 [SMILES: COc1cccc2c1C(=O)c1c(O)c3c(c(O)c1C2=O)C[C@@](O)(C(=O)CO)C[C@@H]3OC1C[C@H](NC(=O)OC(Cc2cn(CCCCCC[P+](c3ccccc3)(c3ccccc3)c3ccccc3)nn2)c2ccc(NC(=O)C(Cl)Cl)cc2)[C@H](O)[C@H](C)O1 ; [Br-]]

(3)

Figure 24:
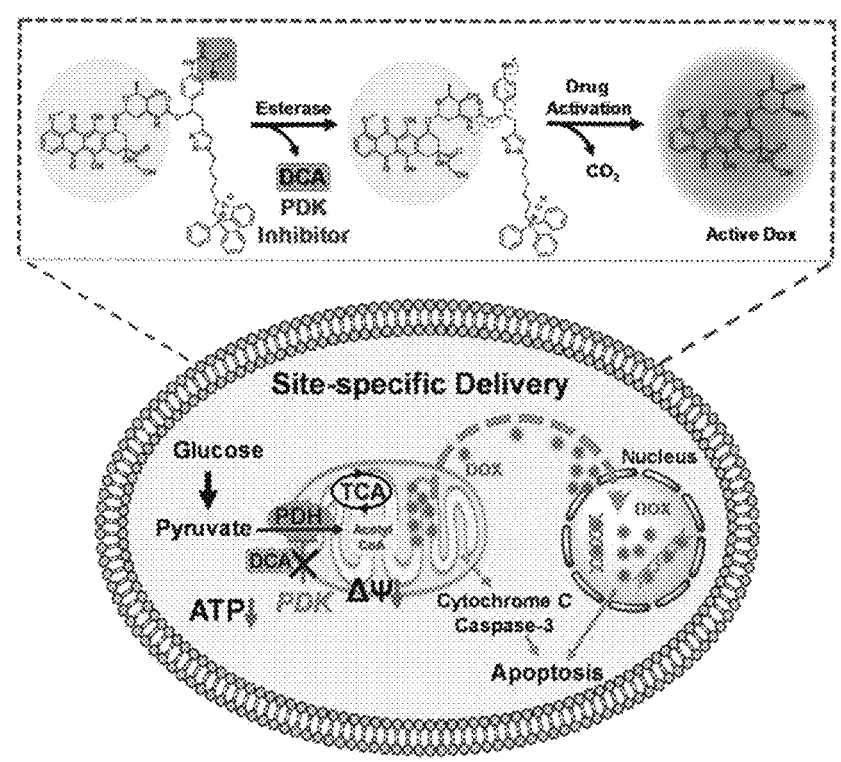
FIG. 24 shows the mechanism of action of the anticancer prodrug of the present invention (DCA, dichloroacetic acid; PDK, pyruvate dehydrogenase kinase; PDH, pyruvate dehydrogenase complex; TCA, tricarboxylic acid cycle; Dox, doxorubicin; ATP, adenosine triphosphate; ψ, mitochondrial membrane potential).

After accumulation in cancer cell mitochondria, the prodrug of the present invention becomes activated by carboxylesterase enzymes to release DCA and DOX. The released DCA (PDK inhibitor) shifts the aerobic glycolysis characteristic (the Warburg effect) of cancerous environments to oxidative phosphorylation (OXPHOS). The free Dox produced via self-immolation in the mitochondria then translocates over time to the nucleus where it mediates its function, and as a result, the growth of drug-resistant tumors can be effectively inhibited, achieving significantly improved anticancer effects. This process is depicted in the mechanism of action of the prodrug (FIG. 24).

The present invention will be explained in more detail with reference to the following examples. However, it will be obvious to those skilled in the art that these examples are merely for illustrative purposes and are not intended to limit the scope of the present invention.

Experimental Methods

Synthesis and Characterization

All chemicals and solvents used for synthesis were purchased from Sigma-Aldrich, Alfa, or TCI-Korea. Moisture sensitive reactions were generally carried out under a blanket of argon gas. NMR spectral analyses were performed on Bruker NMR (500 MHz for 1H, 125 MHz for $^{13}C$) or Varian (400 MHz for $^1H$, 101 MHz for $^{13}C$) instruments at room temperature using $CDCl_3$, MeOD, or DMSO-$d_6$ as the solvents. Chemical shifts (δ) are recorded in ppm and coupling constants are given in Hz. High resolution mass spectra were recorded on an Ion Spec Hi Res ESI mass spectrometer. HPLC analyses were performed on a YL9101S (YL-Clarity) instrument equipped with a reverse-phase column (C18, 5 mm, Waters). A UV-vis detector (475 nm) was used.

Docking and Molecular Dynamics Simulations

The structure of CE1 was obtained from the Protein Data Bank (PDB ID: 1YA81). A grid box was constructed to cover pharmacophores with spacing of 0.2 Å. Docking parameters were set to 50 runs and 2,500,000 energy evaluations for each cycle with Autodock 4.2 and Autodock Tools 1.5.62 using the Lamarckian genetic algorithm. The 10 structures of lowest binding energies obtained in this way were used for further molecular dynamics (MD) simulations.

The force fields for the compounds of interest were generated by density functional theory (DFT) calculations carried out employing the M06 exchange function with the 6-31+G* basis sets, using Gaussian 09. In the MD simulations, the ff14SB and Tip3p water models were employed with 10 independent MD simulations being performed for each compound using the Amber14 package. The SHAKE algorithm was applied to constrain certain bonds, including those involving hydrogen. The Particle-mesh Ewald summation method was used to describe long-range electrostatics. The value of the nonbond cutoff was set to 10 Å. The distance between the system and the box edge was more than 10 Å. Temperature was controlled with a Langevin thermostat using a coupling constant of 1.0 ps. Pressure was controlled by use of a Berendsen barostat with a coupling constant of 2.0 ps. The time step was 1.0 ps. 30 ns MDs were collected in each simulation. After evaluating the equilibration, only the final 20 ns were used to calculate the binding free energies. The binding free energies themselves were obtained using the molecular mechanics generalized-Born surface area (MM/GBSA) method.

Cell Lines and Reagents

Human cancer cell lines and the normal human fibroblast NHDF and IMR-90 cells were purchased from American Type Culture Collection (Rockville, Md., USA) or Korea Cell Line Bank (Seoul, South Korea). The cells were maintained in Dulbecco's modified Eagle's medium supplemented with 10% FBS (GIBCO BRL) at 37° C. in a humidified atmosphere with 5% $CO_2$. Doxorubicin and DCA were obtained from Sigma-Aldrich.

Immunoblotting Assay

Immunoblot analyses were performed using antibodies specific for phosphorylated serine 293 PDH-EI (ab92696), p21$^{Waf1}$ (sc-397), cleaved PARP (5625), cleaved caspase-3 (9664), COX-IV (4850), and Cytochrome c (4280). They were purchased from Abcam (Cambridge, UK), Santa Cruz Biotechnology (Texas, USA) or Cell Signaling Technology (Massachusetts, USA). Anti-tubulin antibodies were obtained from Sigma-Aldrich (St. Louis, USA). Briefly, cells were washed twice in ice-cold PBS and lysed in a radioimmunoprecipitation assay buffer containing 50 mM Tris/HCl (pH 7.5), 150 mM NaCl, 0.1% sodium dodecyl sulfate (SDS), 1% Triton X-100, 1% sodium deoxycholate, and protease inhibitor mixture. After sonification, the lysate was centrifuged, and the supernatant was recovered and loaded onto a 12% SDS-polyacrylamide gel for electrophoresis.

Separation of Cytosolic and Mitochondrial Fractions

Separation of cytosolic and mitochondrial fractions was performed using the Mitochondria Isolation Kit (Thermo Scientific, USA). Briefly, the cells were washed with cold PBS and lysed by 5-cycle freeze-thawing in Mitochondria Isolation Reagent A buffer, containing 10 mM phenylmethylsulfonyl fluoride (PMSF). After incubation on ice for 10 min and the addition of Mitochondria Isolation Reagent B buffer, the lysates were centrifuged at 700×g for 10 min following inverting by treating with Mitochondria Isolation Reagent C buffer. The supernatant was transferred to a new tube, centrifuged at 12 000×g for 15 min at 4° C., and collected as the cytosolic fraction. After adding 500 mL of Mitochondria Isolation Reagent C, the pellet was centrifuged at 12 000×g for 5 min and collected as the mitochondrial fraction.

Cell Viability and Growth Assay

Cells were seeded in 24 well plates at $2 \times 10^5$ cells per well and were allowed to adhere for at least 24 h, growth medium was replaced with medium containing C1 or its analogues at the indicated concentrations and times, and cell viability was assessed via the WST-1 assay (Roche Diagnostics, Laval, QC, Canada). For the colony formation assay, cells were seeded in 6-well plates. After 24 h, cells were maintained in the presence of each probe or vehicle dimethyl sulfoxide (DMSO) for 10 days. Colonies were fixed with methanol for 10 min and stained with 0.05% crystal violet in 20% ethanol.

Measurement of Intracellular ATP, Lactate Levels, and Glucose Uptake

Intracellular ATP levels were measured using an ATP Bioluminescence Assay Kit HSII (Roche Applied Science). Briefly, after the indicated treatment times for the test compound in question, cells were lysed with boiling lysis reagent and the supernatant was collected. 50 mL of the diluted sample were mixed with 50 mL of luciferin/Luciferase reagents. Luminescence was measured using Luminoskan Ascent (Thermo Scientific). Results were normalized to cell number. Intracellular L(+)-lactate level was measured using a lactate assay kit (BioVision). Cells were suspended with lactate assay buffer and incubated in the presence of the reaction mixture for 30 min. The lactate was quantified by measuring the absorbance at 570 nm using a Bio-Rad 680 microplate reader (Bio-Rad). For the glucose uptake assay, $2 \times 10^5$ cells were incubated in the presence of 20 mmol/L of 2-NBDG (2-[N-(7-nitrobenz-2-oxa-1,3-diazol-4-yl)amino]-2-deoxy-d-glucose; N13195; Invitrogen) for 2 h. The cells were re-suspended in cold growth medium and stained with propidium iodide. Samples were maintained on ice and analyzed via flow cytometry (Becton Dickinson).

Immunofluorescence Assay

Cells were seeded on glass chamber slides (Nalgene Nunc) followed by probe treatment. After 48 h, the cells were fixed with 4% formaldehyde, and blocked with 2% bovine serum albumin-PBS for 30 min. The mitochondria were stained using MitoTracker™ Green FM (Invitrogen, USA) for 30 min. Fluorescent images were obtained using a confocal laser scanning microscope (Carl Zeiss MicroImaging, Inc., Germany).

Cellular Uptake of Compounds

To analyze the cellular fluorescence levels upon compound treatment, cells were seeded in plates 1 day before treatment with the compounds. Cells were then treated with each compound for the indicated dose or time course. After the experiment, cells were washed with ice-cold PBS, trypsinized, and centrifuged. The cell pellet was re-suspended in 300 µL of PBS and then analyzed using a multiplate reader (SpectraMAX I3x). The results were normalized according to the number of cells.

In Vivo and Ex Vivo Fluorescent Imaging

To assess tumor target specificity and the organ distribution of C1 in vivo and ex vivo, MCF7 and MCF7/Dox cells were injected subcutaneously into mice. When tumor growth reached a detectable size, the mice were treated with C1 (15 mg/kg/d), doxorubicin (2 mg/Kg/d)+DCA (50 mg/Kg/d), or vehicle (DMSO) by i.v. injection once every 4 days for 30 days. After 15 days of treatment, the animals were euthanized via $CO_2$ asphyxiation. The xenograft tumors were excised and photographed. In vivo fluorescence images of the mice were recorded and quantified using a Maestro2 instrument (excitation and emission wavelengths: 500 and 650 nm, respectively). The fluorescence images and auto-fluorescence were then deconvoluted using the software provided with the instrument (Maestro software ver.2.4, CRi, Woburn, Mass., USA) using the multiexcitation spectral analysis function.

Assessment of Mitochondrial Membrane Potential

To assess the mitochondrial membrane potential, MCF-7/Dox cells ($5 \times 10^3$ cells) were seeded in glass-bottomed dishes and treated with 5 µM compound C1, C3, DCA, and/or doxorubicin for 48 h. After incubation, the cells were stained with 2 ml of a PBS solution containing 20 µM Mitoview™ 633 (Biotium, USA) and 100 nM Hoechst® 33342 (ThermoFisher, USA) for 30 min at 37° C. with 5% $CO_2$. Fluorescence was detected using a Zeiss LSM 700 confocal laser scanning microscope (Carl Zeiss).

Cell Death Assay

MCF-7/Dox cells ($8 \times 10^5$ cells) were seeded in 60 mm dishes and cultured for 24 h. The cells were treated with 5 µM compound C1, C3, DCA and/or doxorubicin for 48 h. After washing and centrifugation, the harvested cells were stained with the Annexin V/PI Apoptosis Detection kit (BD Biosciences, USA) for 1 min at room temperature. The apoptotic cells were then quantified on a FACSCalibur™ flow cytometer and analyzed using the CELLQUEST™ software (BD Biosciences).

Animal Studies

Five-week-old immunodeficient nude mice (nu/nu) mice (Orient Bio, Inc.) were maintained in pressurized ventilated cages under conditions of repeated controlled illumination (12 h dark; 12 h light) with ad libitum access to sterilized water and food (Cat no: 1314Fort, ALTROMIN company, Germany). MCF-7/Dox cells ($1 \times 10^7$) in 200 mL PBS were injected subcutaneously into each nude mouse. When the tumor volumes reached 80-100 mm³, the mice were randomized into 3 treatment groups; vehicle control (DMSO), Dox+DCA, and C1 (n=8 per group). The mice were injected intraperitoneally with C1 (15 mg/kg/d), Dox (2 mg/Kg/d)+DCA (50 mg/Kg/d), or vehicle (DMSO) once every four days for 3 weeks. Tumor growth was monitored periodically, and the tumor volume (V) was calculated by using V=½× length×(width)². After 15 days of treatment, animals were euthanized by $CO_2$ asphyxiation. The xenograft tumors were excised and photographed. All animal studies were performed with the approval of the Korea University Institutional Animal Care and Use Committee and in accord with the Korean Animal Protection Act.

Hepatotoxicity Assay

Blood samples of each mice were centrifuged at 3,000 rpm for 10 min at 4° C. to produce serum. Then, the activities of ALT and AST in serum were analyzed using the AST and ALT Activity Assay Kits (MAK055, MAK052, Sigma) according to the manufacturer's instructions.

Synthesis of Compounds

The compound C1 represented by Formula 1 and controls C2-C6 were synthesized in accordance with the following scheme S1:

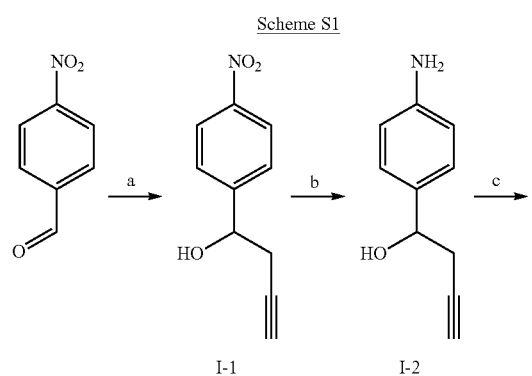

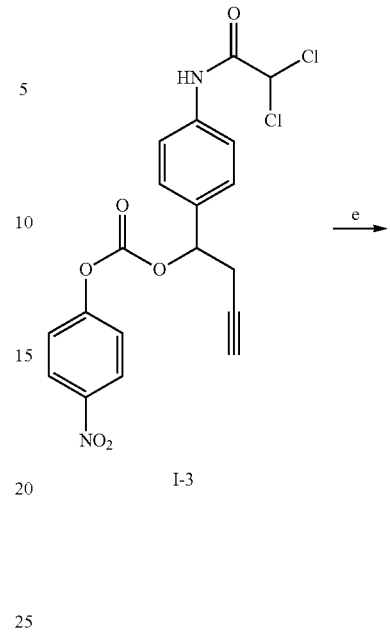

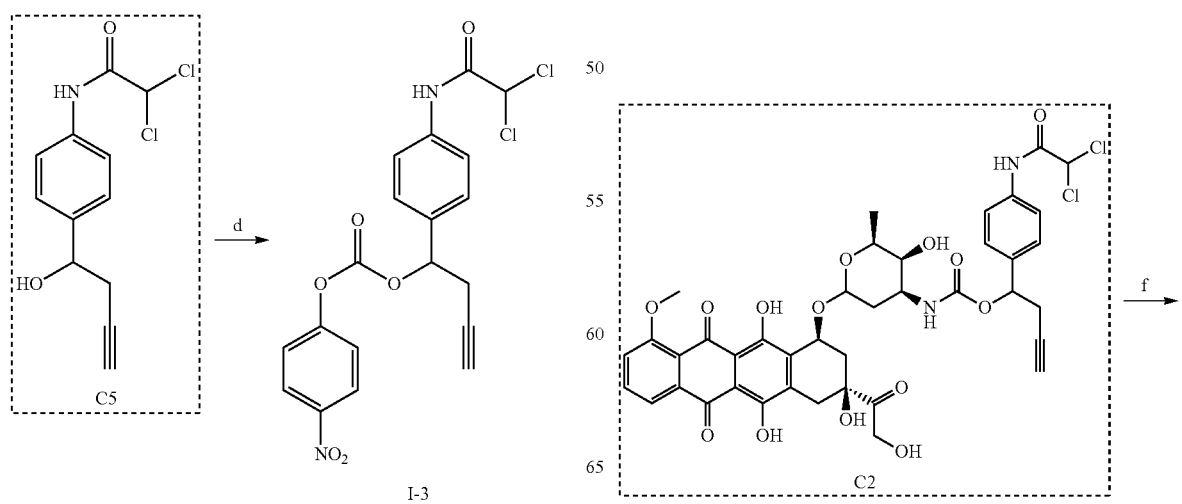

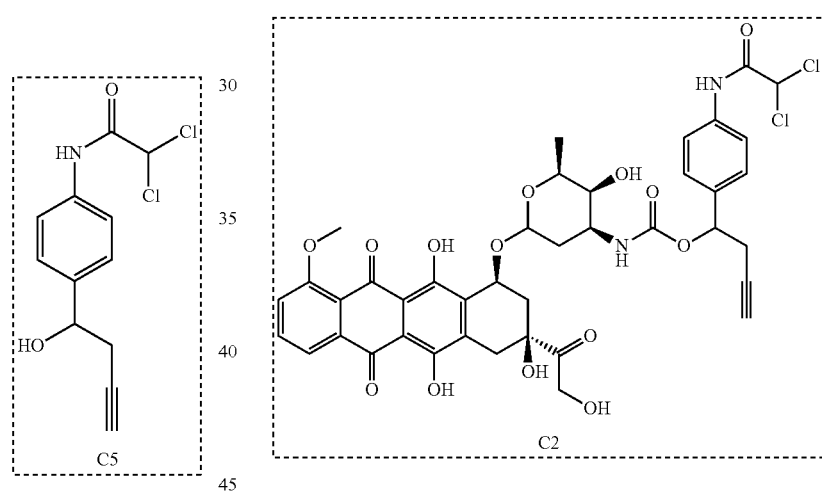

13
-continued
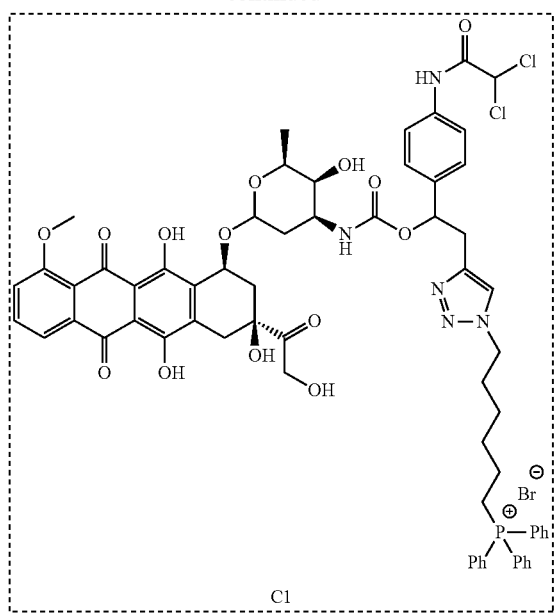
C1
14
-continued
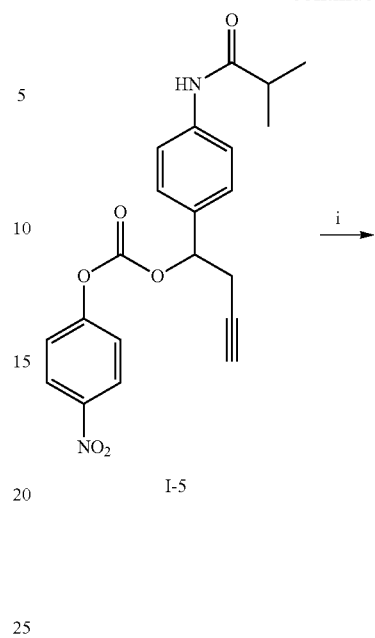
I-5
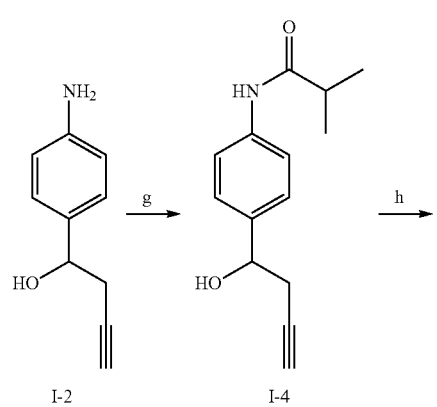
I-2    I-4
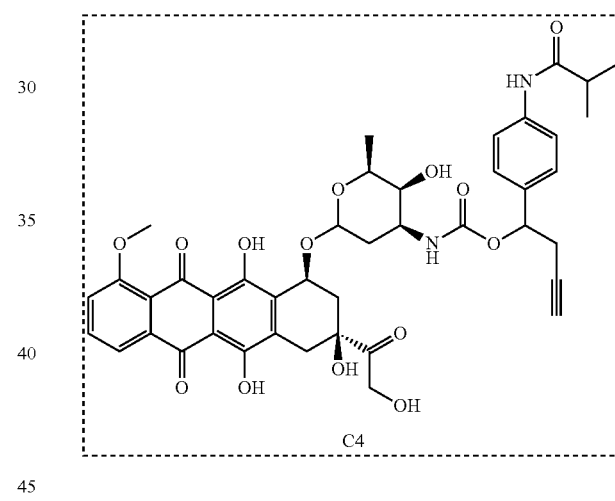
C4
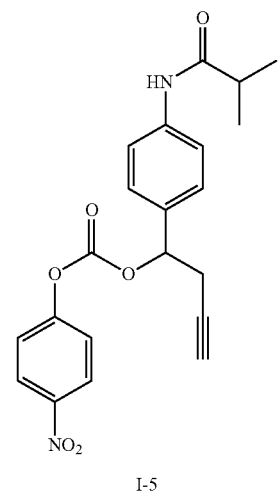
I-5
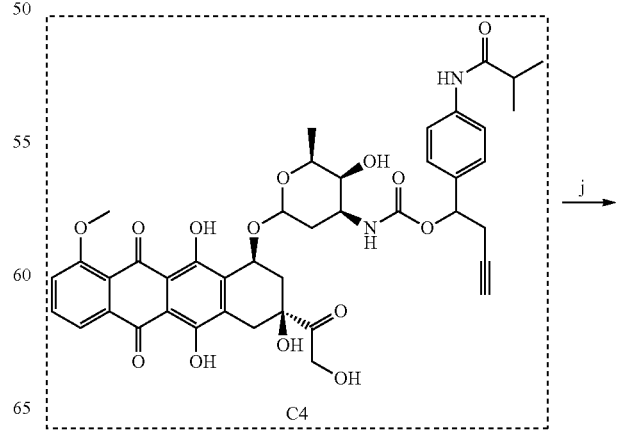
C4

-continued

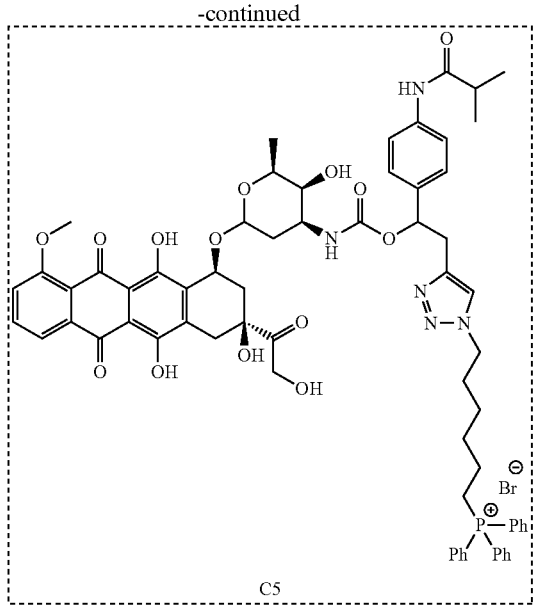

C5

-continued

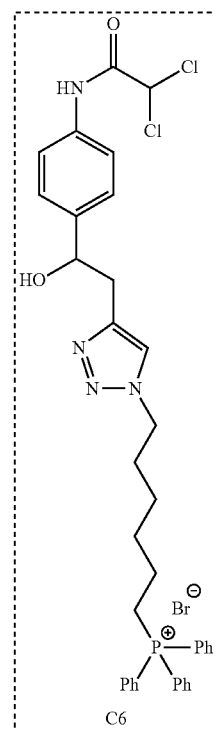

C6

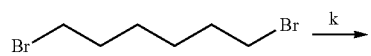

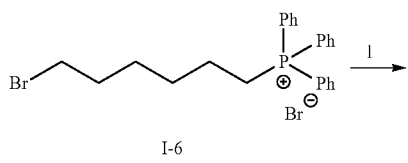

I-6

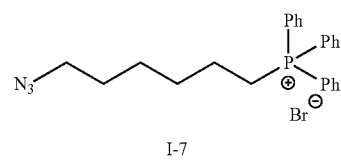

I-7

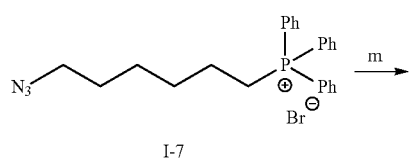

I-7

Reagents and conditions: (a) Propargyl bromide, Al powder, HgCl$_2$, THF, reflux, 95%; (b) Zn/AcOH, DCM, 96%; (c) Dicholoacetyl chloride, DCM, TEA, 0° C., 94%; (d) 4-Nitrophenyl chloroformate, DCM, TEA, 0° C., 93%; (e) Doxorubicin.HCl, DMF, TEA, RT, 95%; (f) 1-7, Sodium ascorbate, MeOH, overnight, 91%; (g) Isobutyryl chloride, DCM, TEA, 0° C., 95%; h) 4-Nitrophenyl chloroformate, DCM, TEA, 0° C., 94%; (i) Doxorubicin.HCl, DMF, TEA, RT, 96%; (j) 1-7, Sod. ascorbate, MeOH, overnight, 87%; (k) PPh$_3$, ACN, reflux overnight, 80%; (l) NaN$_3$, EtOH; H$_2$O, reflux overnight, 86%.

Synthesis of Compound I-1

In a two necked round bottom flask, aluminum powder (1.945 g, 72 mmol) was suspended in anhydrous THF (50 mL). To this slurry, catalytic HgCl$_2$ was added and the mixture was stirred at RT for 15 min. Propargyl bromide (80% in toluene, 78.34 mmol) was added dropwise at 0° C. The mixture was heated at reflux for 2 h at 70° C. After cooling to RT, a solution of p-nitrobenzaldehyde (1.73 g, 11.45 mmol) dissolved in anhydrous THF (30 mL) was added dropwise and the mixture was stirred for an additional 2 h. The crude mixture was poured into 1N aqueous HCl at 0° C. and extracted with ethyl acetate (3×100 mL). The combined organic fractions were washed with water, dried over Na$_2$SO$_4$, filtered, and concentrated under reduced pressure to give I-1 as a light brown solid (1.82 g, 95%).

$^1$H NMR (400 MHz, CDCl$_3$, 28° C.): 2.11 (m, 1H), 2.51 (d, J=3.76 Hz, 1H), 2.66 (m, 2H), 5.00 (m, 1H), 7.58 (m, 2H), 8.23 (d, J=8.72 Hz, 2H). $^{13}$C NMR (125 MHz, 28° C.): 29.4, 71.3, 71.9, 79.4, 123.6, 126.7, 147.5, 149.5. MS (ESI): m/z calcd. for C$_{10}$H$_9$NO$_3$: 191.06. Found: 192.1 [M+1]$^+$.

Synthesis of Compound I-2

I-1 (1.5 g, 7.85 mmol) was suspended in anhydrous dichloromethane (DCM) (30 mL). To this mixture, Zn dust (0.3 g, 6.91 mmol) and AcOH (0.5 mL, 6.99 mmol) were added at RT. Following the addition, the reaction mixture was stirred at RT for 3 h and then treated with first water (120 mL) and then sat. aqueous NaHCO$_3$ (55 mL) slowly. The organic fraction was separated, dried over Na$_2$SO$_4$, and concentrated under vacuum to give crude 1-2 as a brown solid (1.21 g, 96%).

$^1$H NMR (400 MHz, CDCl$_3$, 28° C.): 2.08 (s, 1H), 2.20 (s, 1H), 2.63 (m, 2H), 3.70 (br s, 2H), 4.80 (m, 1H), 6.69 (m, 2H), 7.20 (m, 2H). MS (ESI): m/z calcd. for C$_{10}$H$_{11}$NO: 161.08 Found: 162.02 [M+1]$^+$.

Synthesis of Compound C5

I-2 (0.5 g, 3.1 mmol) was suspended in anhydrous DCM (35 mL) at 0° C. Dichloroacetyl chloride (0.448 mL, 4.65 mmol) was added followed by TEA (0.648 mL, 4.65 mmol). The resulting mixture was stirred for an additional 3 h. After this time, the reaction mixture was washed with water (60 mL). The organic fractions were dried over Na$_2$SO$_4$, separated and concentrated under vacuum. The crude mixture was purified by column chromatography over silica gel (ethyl acetate/DCM 2/8) to obtain the product as light orange solid (0.79 g, 94%).

$^1$H NMR (400 MHz, CDCl$_3$, 28° C.): 2.08 (t, J=1.98 Hz, 1H), 2.36 (d, J=2.7 Hz, 1H), 2.64 (m, 2H), 4.88 (m, 1H), 6.04 (s, 1H), 7.42 (d, J=6.3 Hz), 7.56 (d, J=6.45 Hz, 2H). $^{13}$C NMR (125 MHz, CDCl$_3$, 28° C.): 29.4, 86.8, 71.3, 71.7, 80.3, 120.2, 123.0, 126.5, 126.7, 135.8, 139.8, 161.8. MS (ESI): m/z calcd. for C$_{12}$H$_{11}$Cl$_2$NO$_2$: 271.02 Found: 272.1 [M+1]$^+$.

Synthesis of Compound I-3

C5 (0.2 g, 0.735 mmol) was suspended in anhydrous DCM (25 mL) at RT. 4-Nitrophenyl chloroformate (0.17 g, 0.845 mmol) was added, followed by the dropwise addition of TEA (0.12 mL, 0.88 mmol). The mixture was stirred at RT for an additional 2 h. The solvent was evaporated under reduced pressure and the crude material obtained in this way was purified by column chromatography (MC) to yield 1-3 as colorless oil (0.27 g, 93%).

$^1$H NMR (400 MHz, CDCl$_3$, 28° C.): 2.06 (t, J=1.95 Hz, 1H), 2.90 (m, 2H), 5.80 (m, 1H), 6.50 (s, 1H), 7.36 (d, J=6.93 Hz, 2H), 7.48 (d, J=6.4 Hz, 2H), 7.63 (m, J=6.4 Hz, 2H), 8.16 (m, 1H), 8.26 (d, J=6.93 Hz, 2H). $^{13}$C NMR (100 MHz, CDCl$_3$, 28° C.): 26.6, 31.2, 66.9, 71.8, 78.4, 78.6, 115.8, 120.5, 121.9, 125.5, 126.4, 127.9, 134.8, 137.1, 145.6, 151.8, 155.5, 162.0. MS (ESI): m/z calcd. for C$_{19}$H$_{14}$Cl$_2$N$_2$O$_6$: 436.02 Found: 437.2 [M+1]$^+$.

Synthesis of Compound C2

I-3 (0.1 g, 0.25 mmol) was suspended in anhydrous dimethylformamide (10 mL) in a single necked round bottom flask. Doxorubicin.HCl (0.160 g, 0.275 mmol) was added followed by TEA (0.55 mL, 0.75 mmol). The mixture was stirred at RT for additional 1 h. At this time, the solvent was removed under reduced pressure at <40° C. The crude material obtained in this way was purified by column chromatography (silica gel, MeOH/DCM, 2-5%) to yield product C2 as a red powder (0.202 g, 95%).

$^1$H NMR (400 MHz, CDCl$_3$, 28° C.): 1.28 (m, 3H), 1.77 (m, 2H), 1.94 (m, 2H), 2.03 (m, 1H), 2.28 (m, 1H), 2.3 (m, 1H), 2.67 (m, 2H), 3.00 (m, 2H), 3.24 (m, 1H), 3.60 (m, 1H), 3.82 (m, 1H), 4.06 (m, 4H), 4.47 (m, 1H), 4.72 (m, 2H), 5.25 (m, 2H), 5.48 (m, 1H), 5.66 (m, 1H), 6.00 (m, 1H), 7.30 (m, 3H), 7.38 (m, 1H), 7.48 (m, 2H), 7.78 (m, 1H), 8.02 (m, 1H), 8.16 (m, 1H). $^{13}$C NMR (100 MHz, CDCl$_3$, 28° C.): 16.9, 26.6, 29.8, 30.2, 33.9, 35.8, 47.1, 56.8, 65.5, 65.6, 66.9, 67.0, 67.6, 69.3, 69.6, 71.1, 73.9, 76.5, 77.4, 79.5, 100.8, 111.4, 111.7, 111.8, 120.0, 120.2, 120.3, 120.4, 127.3, 127.4, 133.7, 136.0, 136.6, 155.0, 166.1, 186.8, 187.2, 214.0. MS (ESI): m/z calcd. for C$_{40}$H$_{38}$Cl$_2$N$_2$O$_{14}$: 840.17 Found: 863.15 [M+23]$^+$.

Synthesis of Compound C1

To a solution of C2 (0.1 g, 0.11 mmol) and 1-7 (0.05 g, 0.12 mmol) in MeOH (10 mL) containing 5% water, copper sulfate (9 mg, 0.05 mmol), and L-sodium ascorbate (0.028 mg, 0.14 mmol) were added. The mixture was stirred at RT overnight. After this time, EDTA (20 mg, 0.07 mmol) in water was added at RT and the mixture was stirred for 30 min. The reaction mixture was evaporated under reduced pressure and purified by column chromatography (silica gel, 5% MeOH/DCM) to obtain compound C1 as a red powder (0.133 g, 91%).

$^1$H NMR (500 MHz, DMSO-d6, 28° C.): 1.10 (m, 5H), 1.41 (s, 1H), 1.45 (m, 6H), 1.63 (m, 2H), 1.84 (m, 1H), 2.12 (m, 2H), 2.9 (s, 1H), 3.02 (m, 2H), 3.46 (m, 3H), 3.63 (s, 1H), 3.96 (s, 3H), 4.15 (m, 3H), 4.54 (m, 1H), 4.72 (m, 1H), 4.84 (s, 1H), 4.91 (m, 1H), 5.20 (s, 1H), 5.41 (m, 1H), 5.68 (m, 1H), 5.75 (s, 1H), 6.59 (m, 1H), 6.86 (m, 1H), 7.15 (m, 2H), 7.42 (m, 1H), 7.50 (m, 1H), 7.64 (m, 1H), 7.81 (m, 14H), 7.91 (m, 5H), 10.66 (m, 1H). $^{13}$C NMR (125 MHz, DMSO-d6, 28° C.): 17.4, 17.5, 20.4, 20.8, 21.9, 21.9, 25.2, 29.5, 29.6, 29.6, 29.8, 32.6, 49.3, 55.4, 56.9, 57.0, 60.9, 64.1, 64.2, 67.6, 67.6, 74.0, 75.3, 110.9, 118.5, 118.6, 119.2, 119.3, 119.7, 119.8, 119.8, 123.5, 127.3, 127.4, 130.6, 130.7, 133.9, 134.0, 134.0, 135.3, 137.2, 142.7, 154.9, 155.0, 155.0, 156.4, 161.1, 162.0186.6, 214.3. MS (ESI): m/z calcd. For C$_{64}$H$_{65}$Cl$_2$N$_5$O$_{14}$P$^+$: 1230.11 Found: 1230.35 [M$^+$].

Synthesis of Compound I-4

I-2 (0.5 g, 3.1 mmol) was suspended in anhydrous DCM (35 mL) at 0° C. Isobutyryl chloride (0.388 mL, 3.72 mmol) was added followed by TEA (0.648 mL, 4.65 mmol) and the mixture was stirred for additional 3 h. After this time, the reaction mixture was washed with water (60 mL), the organic fractions were collected and dried over Na$_2$SO$_4$, separated, and concentrated under vacuum. The resulting crude mixture was purified by column chromatography over silica gel (ethyl acetate/DCM 2/8) to yield the desired product as a light brown solid (0.68 g, 95%); $^1$H NMR (400 MHz, CDCl$_3$, 28° C.): 1.25 (d, J=5.4 Hz, 6H), 2.5 (m, 1H), 2.35 (d, J=2.4 Hz, 1H), 2.51 (m, 1H), 2.61 (m, 2H), 4.85 (m, 1H), 7.17 (s, 1H), 7.31 (d, J=6.4 Hz, 2H), 7.52 (d, J=6.2 Hz, 2H). MS (ESI): m/z calcd. for C$_{14}$H$_{17}$NO$_2$: 231.13 Found: 232.15 [M+1]$^+$.

Synthesis of Compound I-5

Compound I-5 was synthesized according to the procedure used to prepare 1-3, but starting from 1-4 (0.2 g, 0.735 mmol); this gave 1-5 in good yield (0.32 g, 94%).

$^1$H NMR (400 MHz, CDCl$_3$, 28° C.): 1.26 (d, J=5.1 Hz, 6H), 2.04 (m, 1H), 2.51 (m, 1H), 2.90 (m, 2H), 5.79 (m, 1H), 7.21 (m, 1H), 7.35 (m, 4H), 7.57 (m, 2H), 8.26 (m, 2H). MS (ESI): m/z calcd. for C$_{21}$H$_{20}$N$_2$O$_6$: 396.39 Found: 397.12 [M+1]$^+$.

Synthesis of Compound I-6

To 1,6-dibromohexane (1 g, 4.14 mmol) in 100 mL dry ACN was added triphenylphosphine (1.08 g, 4.14 mmol) and the resulting mixture was heated at 70° C. overnight. After this time, the volatiles were removed under reduced pressure. The crude product obtained in this way was recrystallized from MeOH to give I-5 (1.40 g, 86%) as a white solid.

$^1$H NMR (400 MHz, CDCl$_3$, 28° C.): 1.14 (m, 2H), 1.71 (m, 3H), 1.80 (m, 2H), 2.25 (m, 1H), 3.37 (m, 2H), 3.83 (m, 2H), 7.69 (m, 6H), 7.70-7.87 (m, 9H). $^{13}$C NMR (100 MHz, CDCl$_3$, 28° C.): 22.4, 22.4, 22.8, 27.6, 29.3, 29.4, 34.0, 117.8, 118.4, 130.4, 130.5, 133.5, 133.6, 133.6, 135.0, 135.1. MS (ESI): m/z calcd. for C$_{24}$H$_{27}$BrP$^+$: 388.19 Found: 388.20 [M$^+$].

Synthesis of Compound I-7

I-6 (0.5 g, 1.17 mmol) and sodium azide (0.084 g, 1.29 mmol) were taken up in 5 mL dry DMF and the resulting mixture was stirred overnight at 60° C. After this time, the volatiles were evaporated off at <40° C. under reduced pressure. The resulting crude materials was used as such for the next step.

MS (ESI): m/z calcd. for $C_{24}H_{27}N_3P^+$: 425.10 Found: 425.15 [M$^+$].

Synthesis of Compound C4

Compound C4 was synthesized by following the same procedure used to obtain compound C2. Thus, starting with 1-5 (0.1 g, 0.25 mmol), compound C4 (0.195 g, 96%) was obtained as a red powder.

$^1$H NMR (400 MHz, CDCl$_3$, 28° C.): 1.21 (m, 9H), 1.75 (m, 2H), 1.90 (m, 1H), 2.02 (m, 1H), 2.24 (m, 2H), 2.42 (m, 1H), 2.64 (m, 2H), 2.89 (m, 1H), 3.16 (m, 1H), 3.48 (m, 1H), 3.62 (m, 1H), 3.71 (m, 1H), 3.81 (m, 1H), 4.03 (m, 4H), 4.48 (s, 1H), 4.70 (m, 2H), 5.24 (m, 2H), 5.48 (m, 1H), 5.62 (m, 1H), 7.23 (m, 2H), 7.38 (m, 5H), 7.77 (m, 1H), 7.48 (m, 1H). $^{13}$C NMR (100 MHz, CDCl$_3$, 28° C.): 17.0, 19.7, 19.8, 26.6, 30.3, 34.0, 35.7, 36.7, 47.1, 56.8, 65.7, 67.5, 69.6, 69.8, 71.0, 74.0, 74.0, 76.7, 76.9, 79.7, 101.0, 111.6, 118.6, 119.9, 120.8, 127.2, 127.3, 133.7, 135.4, 135.9, 138.2, 155.0, 155.6, 156.3, 161.1, 175.8, 186.6, 187.7. MS (ESI): m/z calcd. for $C_{42}H_{44}N_2O_{14}$: 800.28 Found: 823.40 [M$^+$23]$^+$.

Synthesis of Compound C3

Compound C3 was synthesized using same procedure used to obtain compound C1. Thus, starting with compound C4 (0.1 g, 0.123 mmol), compound C3 (0.13 g, 87%) was isolated as a red powder.

$^1$H NMR (400 MHz, DMSO-d6, 28° C.): 1.04 (m, 10H), 1.48 (m, 5H), 1.64 (m, 2H), 1.83 (m, 1H), 2.13 (m, 2H), 2.58 (m, 1H), 2.94 (m, 2H), 3.14 (m, 4H), 3.51 (m, 4H), 3.63 (m, 2H), 3.95 (m, 3H), 4.21 (m, 4H), 4.56 (m, 2H), 4.74 (m, 1H), 4.85 (m, 2H), 5.29 (m, 1H), 5.43 (m, 1H), 5.66 (m, 1H), 6.84 (m, 1H), 7.16 (m, 2H), 7.63 (m, 3H), 7.77 (m, 16H), 9.85 (m, 1H). $^{13}$C NMR (100 MHz, DMSO-d6, 28° C.): 17.6, 17.6, 20.0, 20.1, 20.1, 20.1, 22.1, 22.2, 22.2, 22.2, 25/4, 25.5, 29.9, 30.0, 33.1, 35.4, 35.4, 47.6, 49.7, 49.6, 49.6, 64.3, 64.3, 68.7, 744, 75.5, 111.2, 116.7, 118.6, 120.5, 123.5, 127.2, 127.4, 130.8, 130.9, 134.1, 134.1, 134.2, 134.2, 135.5, 139.4, 143.0, 143.1, 155.1, 155.2, 155.3, 156.6, 156.7, 161.3, 161.4, 175.7, 175.8, 187.0, 214.5. MS (ESI): m/z calcd. for $C_{66}H_{71}N_5O_{14}P^+$: 1188.47 Found: 1188.50 [Mt].

Synthesis of Compound C6

Compound C6 was synthesized following the same procedure used to obtain C1. Thus, starting with C5 (0.12 g, 0.44 mmol) and 1-7 (0.205 g, 0.52 mmol), compound C6 (0.25 g, 86%) was isolated as a light yellow solid.

$^1$H NMR (400 MHz, CD$_3$OD, 28° C.): 1.18 (m, 3H), 1.52 (m, 7H), 3.01 (m, 1H), 3.12 (m, 1H), 3.41 (m, 2H), 4.27 (m, 2H), 6.44 (s, 1H), 7.20 (m, 2H), 7.47 (m, 3H), 7.80 (m, 16H). $^{13}$C NMR (100 MHz, CD$_3$OD, 28° C.): 19.5, 19.5, 20.0, 20.5, 20.6, 23.7, 28.0, 28.0, 28.1, 33.5, 48.1, 65.5, 71.1, 116.7, 117.5, 118.2, 121.8, 125.1, 128.7, 128.8, 132.0, 132.1, 133.5, 135.2, 139.3, 142.5, 161.2. MS (ESI): m/z calcd. for $C_{36}H_{38}N_4O_2$: 659.21 Found: 659.32 [M$^+$].

Results and Discussion

Figure 1:
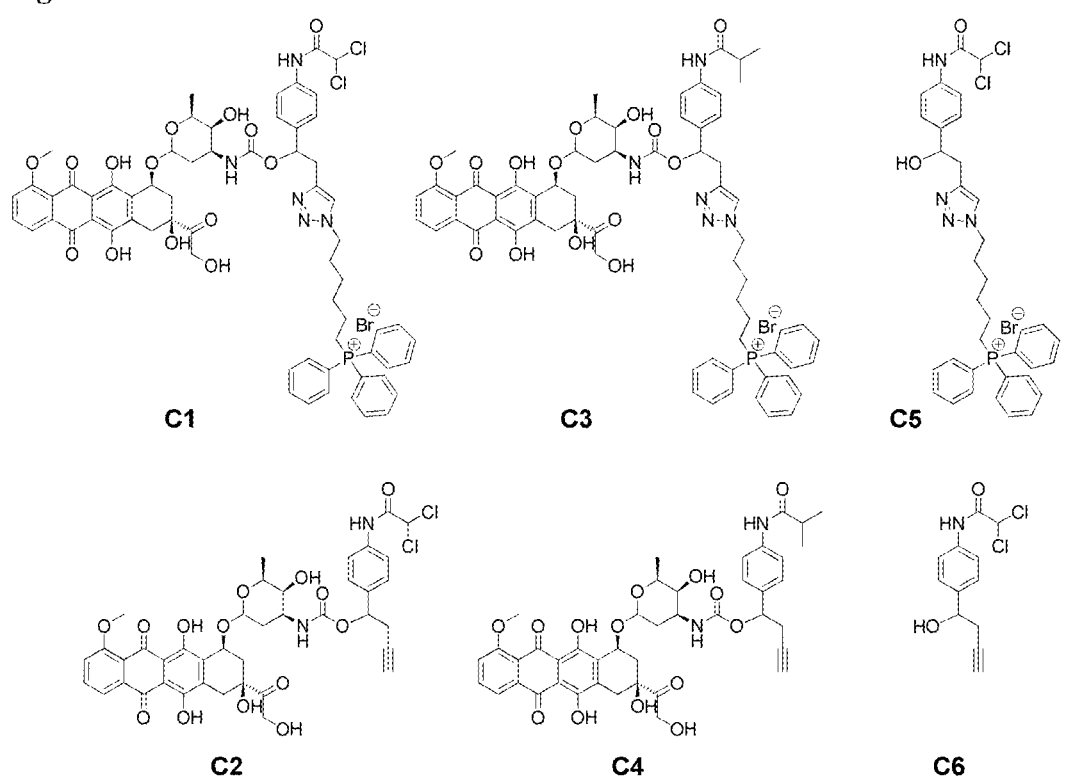
FIG. 1 shows chemical structures of compound C1 and controls (C2-$C_6$)

The present invention provides a small-molecule targeted drug conjugate, compound C1, that circumvents drug resistance in MDR cells even at low doses. Compound C1 of the present invention contains a doxorubicin (Dox) moiety reversibly connected to a dichloroacetic acid (DCA) subunit, as well as a triphenylphosphonium (TPP) mitochondrial targeting group. Control compounds contain some, but not all, of these presumably key subunits (FIG. 1).

Dox is an anthracycline antibiotic that is the standard of care for many cancer patients. However, it suffers from drug efflux mediated by various drug transporter proteins and in many cases fails to produce curative clinical outcomes. DCA is a PDK inhibitor that, when incorporated into a larger structure in the form of, e.g., an amide derivative, offers the possibility of sustained drug release. In the context of conjugate C1, the DCA moiety is attached in the form of an aniline amide that was expected to be susceptible to enzymatic-induced release. The associated bond cleavage was expected to fulfill a dual role. First, it would provide a metabolic modulator (DCA) that would weaken drug resistance mechanisms. Second, it would induce a cascade of reactions to release free Dox that would be finally translocated from mitochondria to the nucleus to evade the various Dox-refractory mechanisms in the initial stages of the drug activation process. Usually, cancer cells have higher mitochondrial membrane potentials ($\Delta\psi_m$=220 mV) than normal cells (140 mV). A tethered lipophilic TPP cation was included in conjugate C1 to provide the predicative mitochondrial targeting. Because of its multicomponent nature, conjugate C1 was expected to provide a greater therapeutic benefit than Dox alone, combinations of Dox+DCA, and even alternative Dox-based targeting strategies. Experimental support for these suggestions, involving studies of both human cancer cell lines and Dox-resistant murine xenograft tumor models, is provided below. The results presented here suggest that the combination of metabolic alternation and subcellular targeting could provide an attractive strategy for addressing chemoresistant tumors.

Design and Synthesis of Compounds

From a synthetic perspective, the challenge of the present invention involved linking a recognized metabolic mediator, DCA, with an active drug with a recognized resistance profile (Dox) through a cleavable linker that would permit further tagging with a cancer targeting entity. It was believed that the resulting molecular construct would need to be stable yet capable of releasing both the DCA and Dox moieties in response to a single triggering event. With these considerations in mind, as a target for synthesis, an intermediate, 1-2 (see Scheme S1), was chosen that could be used to link a DCA subunit to a Dox-based construct while concurrently expressing an alkyne functionality that would allow for further copper-assisted tagging. 1-2 contains a strongly donating aniline group ($\sigma_p$=−0.66) that could be elaborated to produce amides and carbamates, which are weakly donating (Hammett constant, $\sigma_p$=0.00). In the present invention, the carboxylesterase-based triggering strategy was taken advantage of to effect both Dox and DCA release. Aromatic amides are known to be hydrolyzed by carboxylesterase at the N-terminal position. However, it remained an open question whether the presence of the bulkier dichloromethyl group in derivatives of 1-2 (e.g., compounds C1 and C3; see below) would still allow the compound to fit into carboxylesterase enzymatic active site and undergo cleavage.

Figure 2A:
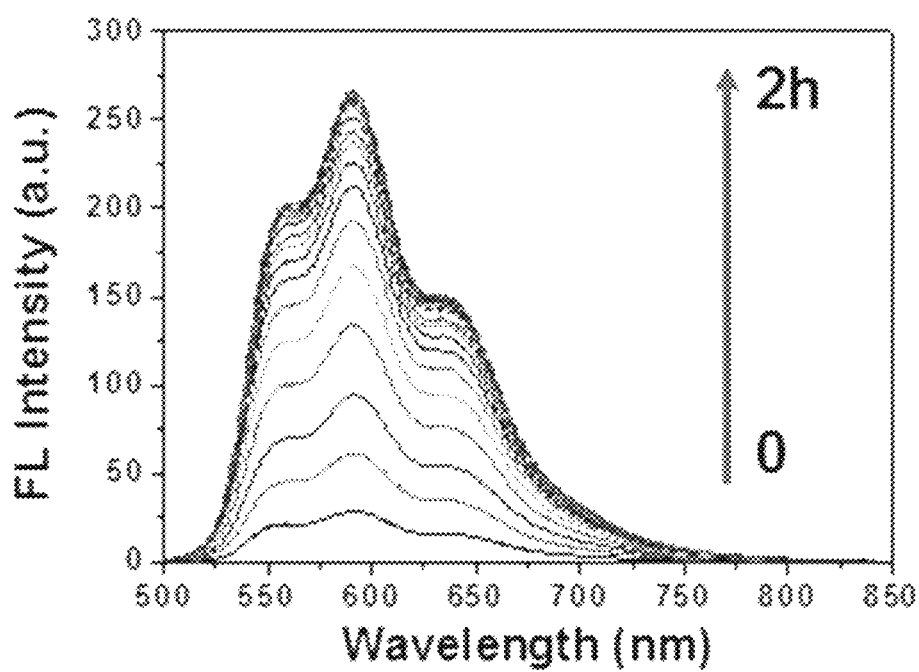
FIG. 2A shows the fluorescence intensity response of C1 (5 µM) seen upon incubation with carboxylesterase (1 U/mL) in phosphate-buffered saline (PBS) (37° C.).
Figure 2B:
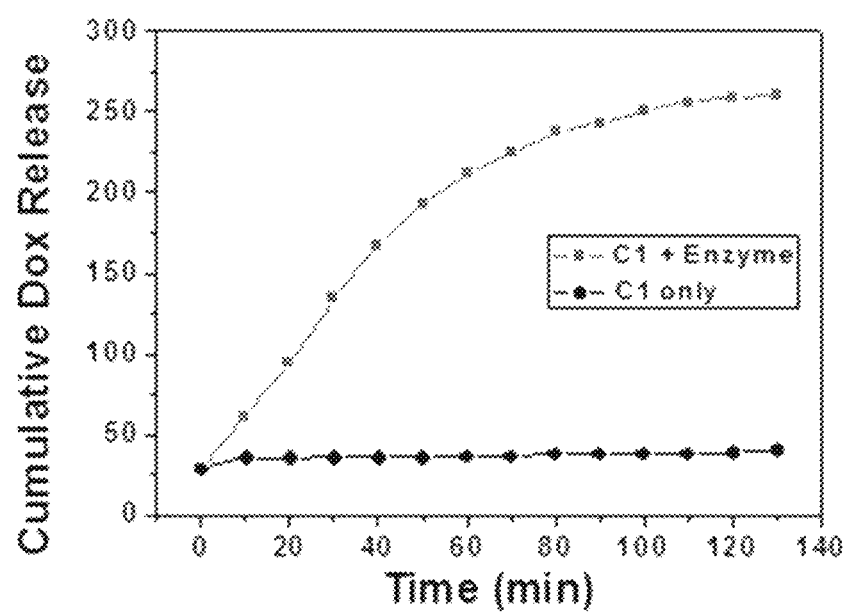
FIG. 2B shows the time-dependent fluorescence enhancement seen upon incubation of C1 with carboxylesterase (1 U/mL) in PBS (37° C.). The change in fluorescence intensity is directly related to active Dox release from C1.
Figure 2C:
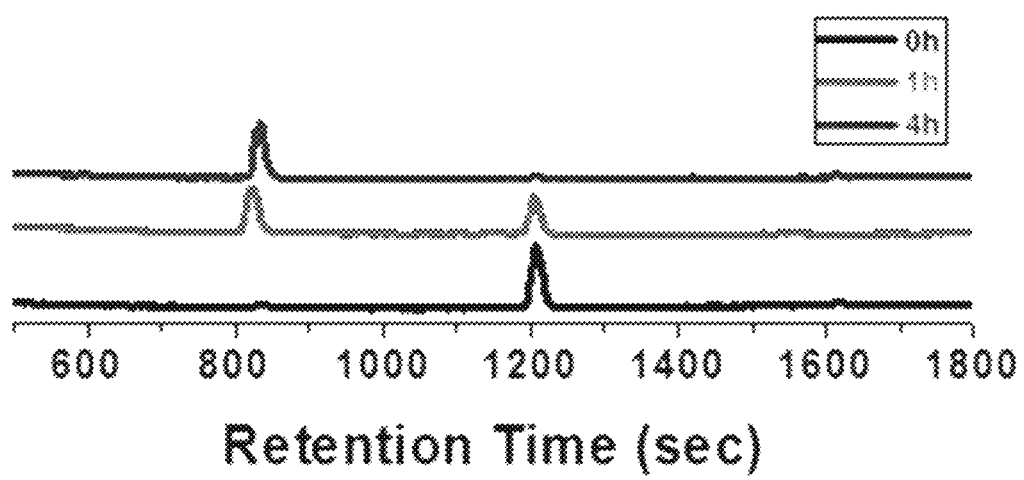
FIG. 2C shows reverse-phase high-performance liquid chromatography (RP-HPLC) curves of C1 treated with esterase at 37° C. for 4 hr.
Figure 6A:
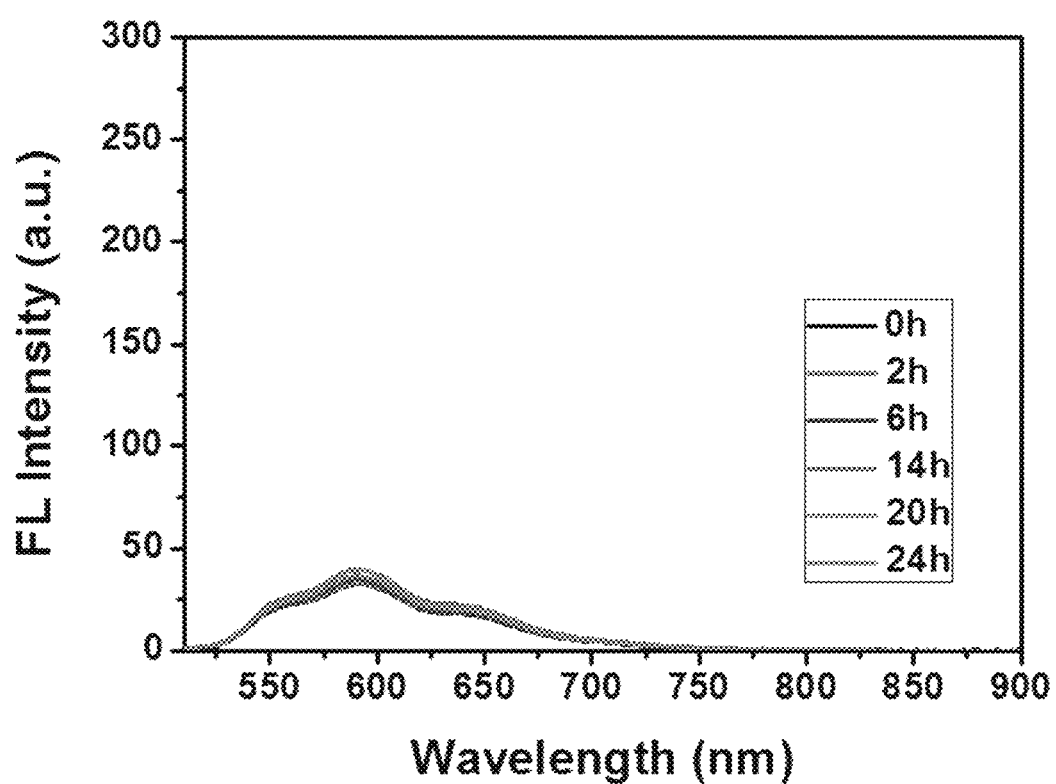
FIG. 6A shows fluorescence intensity of a solution of C1 (5 μM in PBS) recorded at different time points while held at 37° C.
Figure 6B:
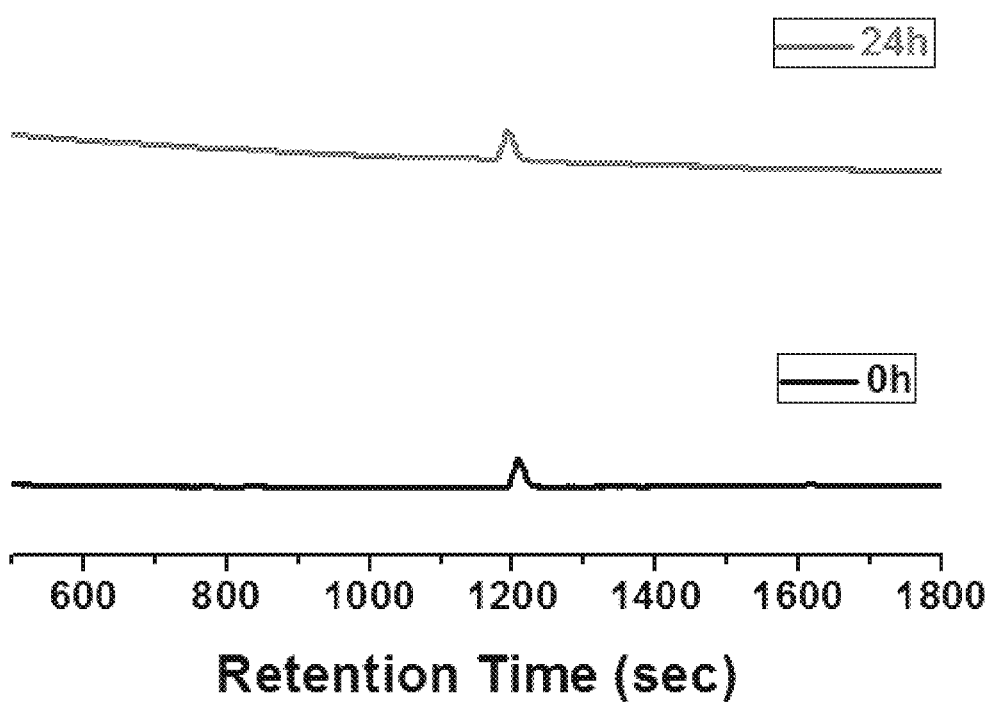
FIG. 6B shows reverse-HPLC curves of C1 recorded 0 and 24 h after incubation in PBS at 37° C.
Figure 7:
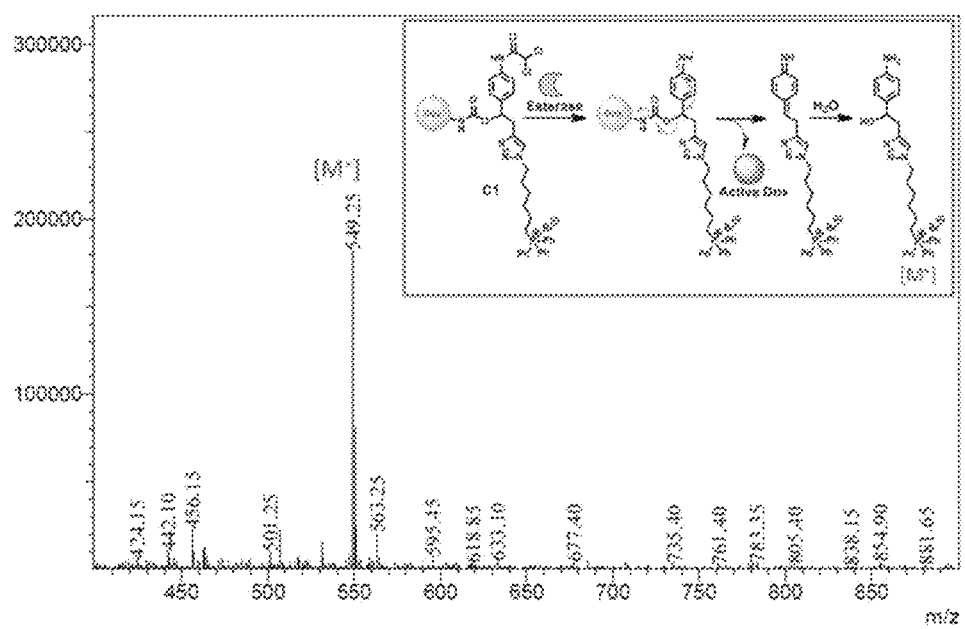
FIG. 7 shows a mass spectrum of the intermediate formed in the reaction of C1 (5 μM) with carboxylesterase (1 U/mL, PBS, 37° C., 4 h), and the proposed mechanism for the formation of the intermediate (inset)
Figure 8:
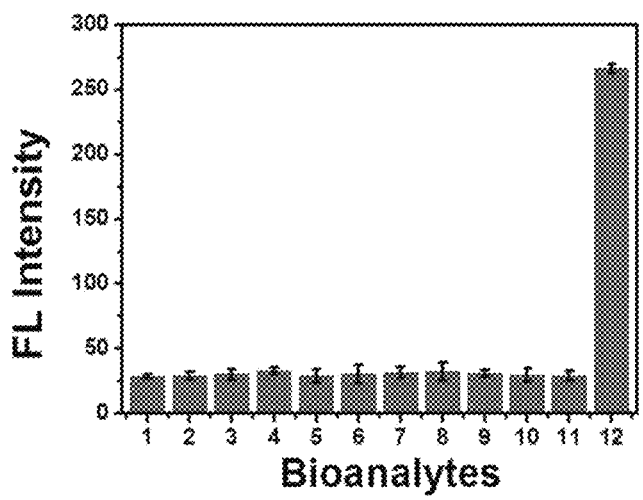
FIG. 8 is a bar diagram representing the fluorescence intensity of C1 (5 μM) recorded at 570 nm after 4 h incubation in the presence or absence of carboxylesterase (1 U/ml), and various biological analytes, including amino acids (100 μM), thiols (10 mM, each), and reactive oxygen species (ROS) (200 μM, each) (Excitation at 470 nm). 1) C1 only, 2) L-proline, 3) L-ascorbic acid, 4) L-glutamic acid, 5) nicotinamide adenine dinucleotide (NADH), 6) pepsin, 7) acetylcholinesterase (AChE), 8) butyrylcholinesterase (BChE), 9) L-glutathione, 10) H$_2$O$_2$, 11) hypochlorite ion (OCl$^-$) 12) C1+esterase.

To gain further insight into the preliminary stability and activation of conjugates containing DCA, Dox, and a TPP cation targeting entity, both the target conjugate C1 and the control system C3 (an analog of C1 lacking the chloromethyl groups present in DCA; cf. FIG. 1) were prepared. These two conjugates were obtained in excellent yield, as shown in Scheme S1. Upon incubation of C1 in phosphate-buffered saline (PBS [pH 7.4]) at 37° C. for 24 hr, no decomposition was observed. This was taken as an augury that C1 would likely prove stable under physiologic conditions (FIGS. 6A and 6B). Conjugate C1 displayed a very weak fluorescence emission at 590 nm (FIG. 2A). On the other hand, exposure of C1 to carboxylesterase (1 U/mL) resulted in scission of the aniline-amide bond and release of Dox from the reactive intermediate, presumably via the 1,6-elimination route characteristic of these kinds of aniline derivatives. This release was accompanied by a strong emission band at 560 nm corresponding to free Dox (FIG. 2A and FIG. 2B). Further support for the release of free Dox under these conditions came from time-dependent fluorescence experiments, HPLC, and liquid chromatography-mass spectrometry (FIG. 2B and FIG. 2C, and FIG. 7). Similar results were observed for conjugate C3 under the same experimental conditions (FIGS. 9A-9D, FIGS. 10A-10B, and FIGS. 11 and 12). To test the reaction of C1 with various other bioanalytes, the fluorescence response in the presence of various amino acids, enzymes, and biomolecules was recorded. Distinct and large fluorescence enhancements in the 590 nm emission feature were observed upon treatment with the esterase but not in its absence. This finding suggests that C1 is an effective substrate for this enzyme and that it may be activated in a selective manner (FIG. 8).

Figure 2D:
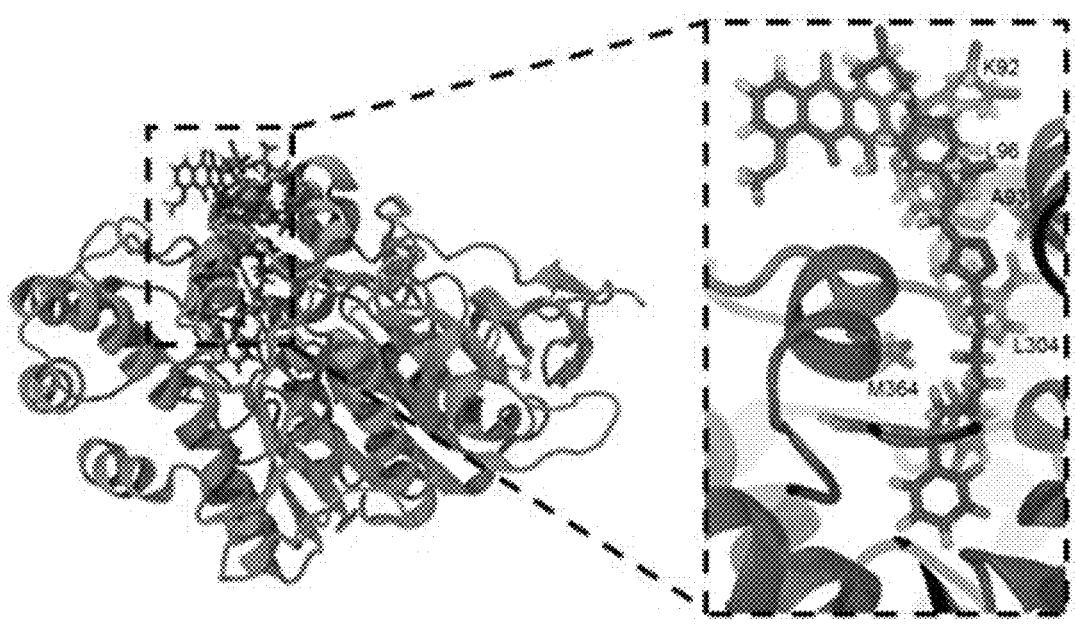
FIG. 2D shows the binding of C1 to human CE1.
Figure 9A:
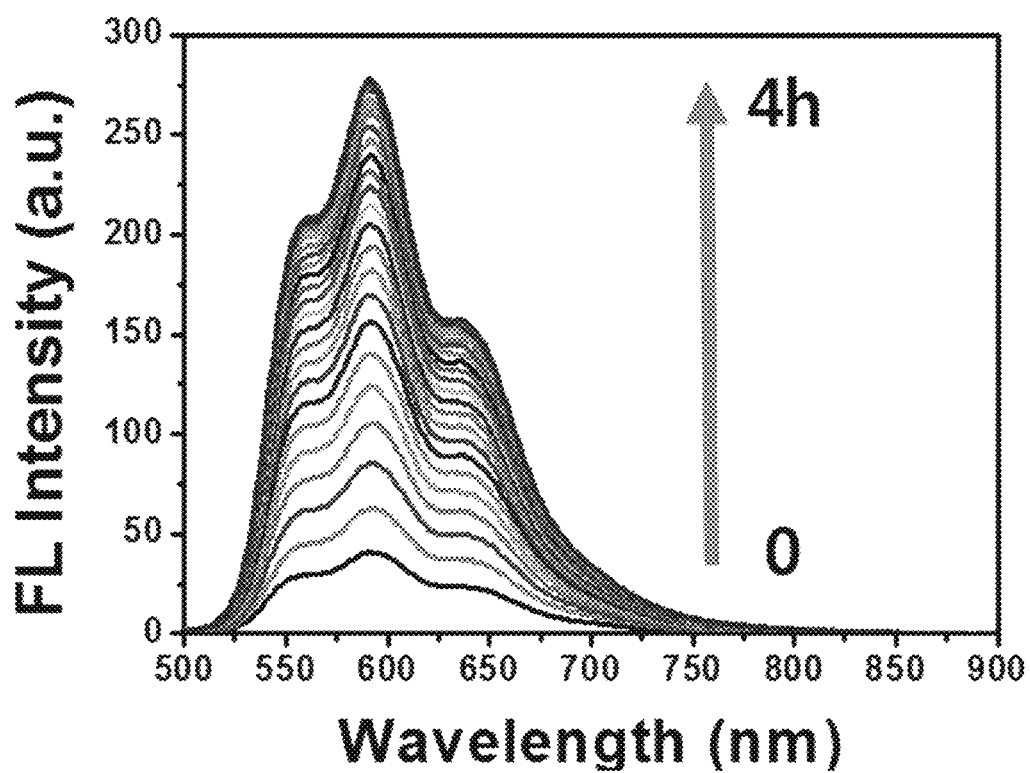
FIG. 9A shows fluorescence intensity response of C3 (5 μM) observed upon incubation with carboxylesterase (1 U/mL) in PBS (37° C.). The maximal fluorescence intensity was recorded after 4 h.
Figure 9B:
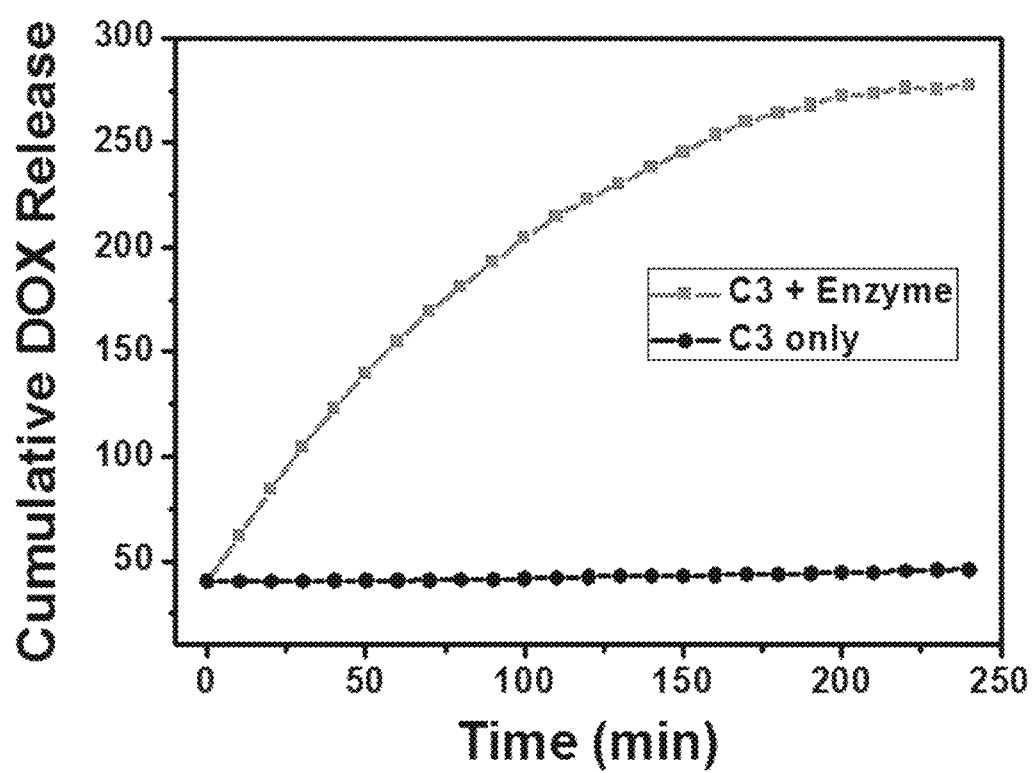
FIG. 9B shows the time-dependent fluorescence enhancement seen upon incubation of C3 with carboxylesterase (1 U/mL) in PBS (37° C.). Note: The change in fluorescence intensity is considered to be proportional to the quantity of active Dox release from C3.
Figure 9C:
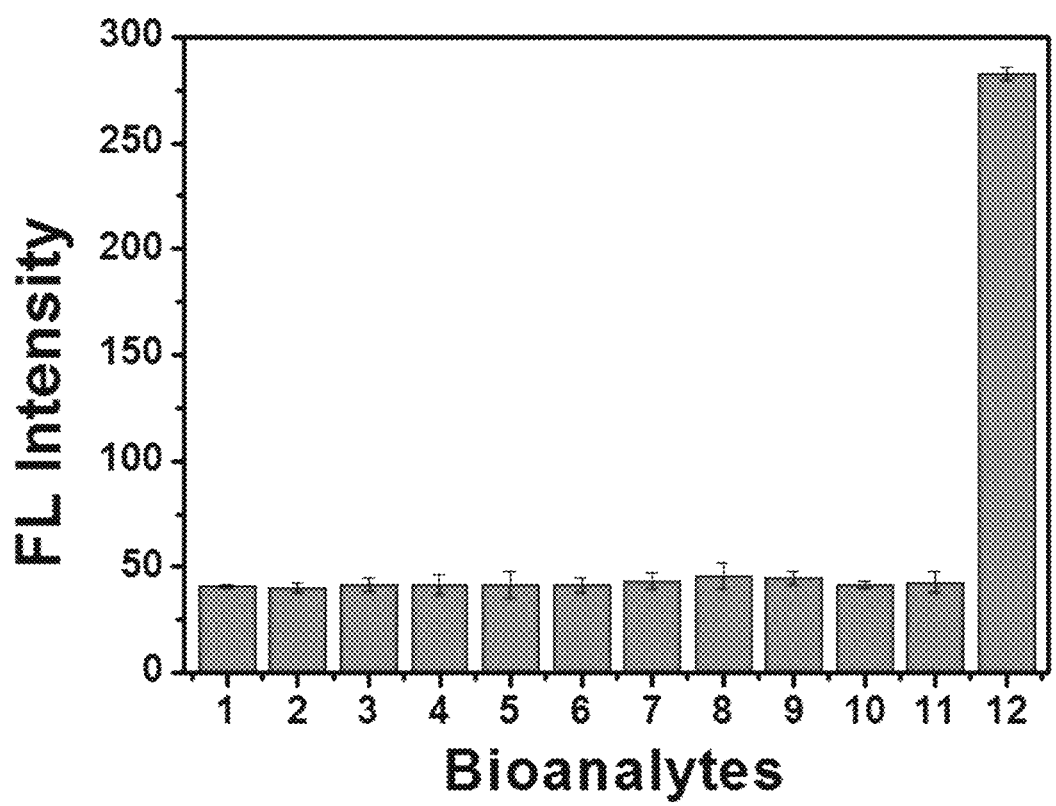
FIG. 9C shows a bar diagram representing the fluorescence response of C3 (5 μM) at 590 nm 4 h after incubation in the presence or absence of carboxylesterase (1 U/mL) and various biological analytes, including amino acids (100 μM), thiols (10 mM, each) and reactive oxygen species (ROS) (200 μM, each) (Excitation at 470 nm). 1) C3 only, 2) L-proline, 3) L-ascorbic acid, 4) L-glutamic acid, 5) NADH, 6) pepsin, 7) AChE, 8) BChE, 9) L-glutathione, 10) H$_2$O$_2$, 11) hypochlorite ion (OCl$^-$), 12) C3+carboxylesterase.
Figure 9D:
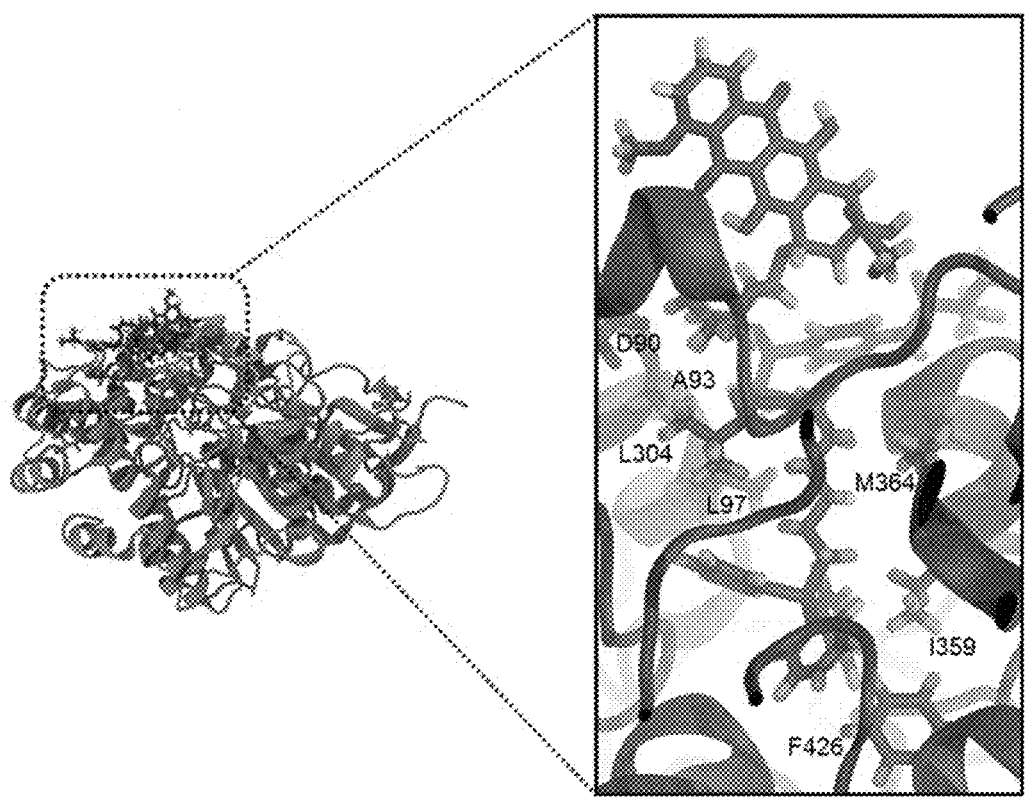
FIG. 9D shows proposed binding between C3 and human CE1.
Figure 13:
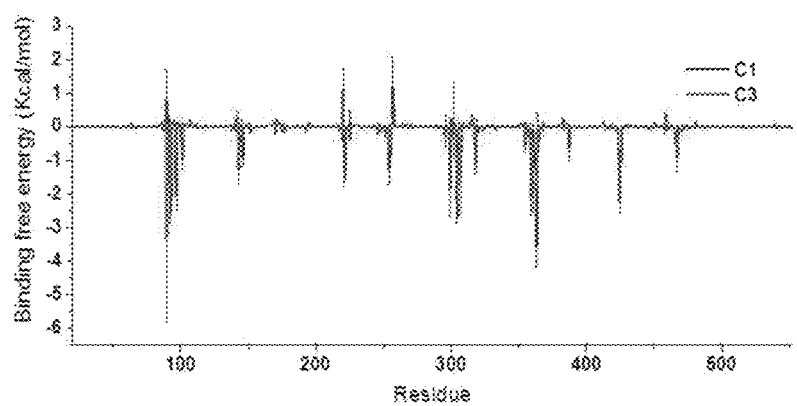
FIG. 13 shows deconvoluted binding free energies for the interactions between C1 and C3 and human CE1.
Figure 14A:
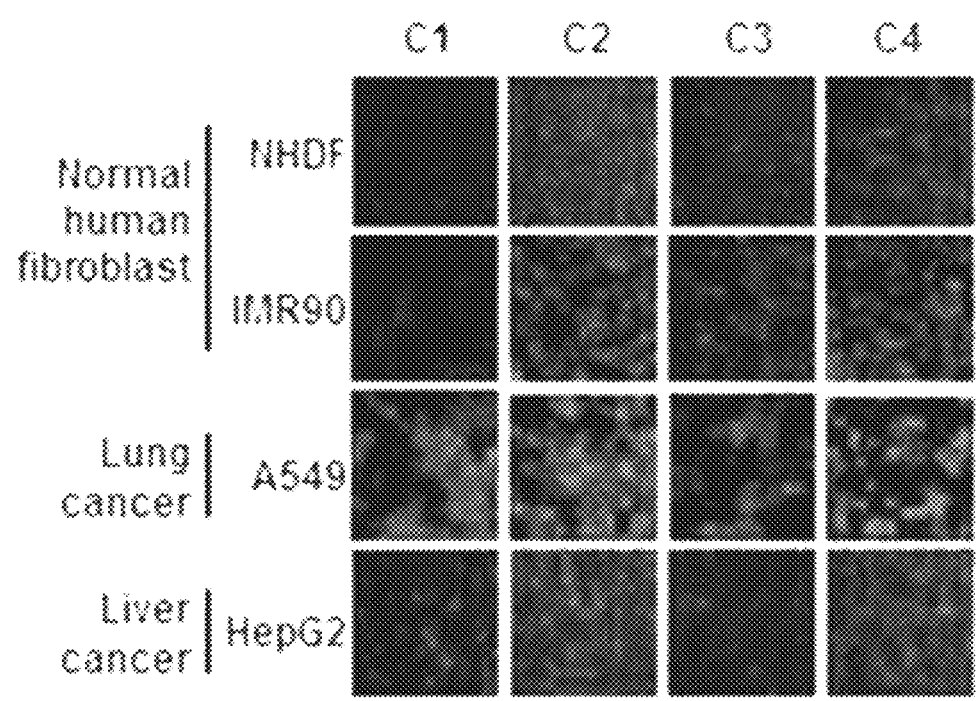
FIG. 14A and FIG. 14B shows comparative analysis of the extent of intracellular uptake of compounds C1-C4 in human normal and cancer cells. Cells were treated with 5 μM of each compound for 6 h. Fluorescence intensities were determined using SpectraMAX 13.
Figure 14B:
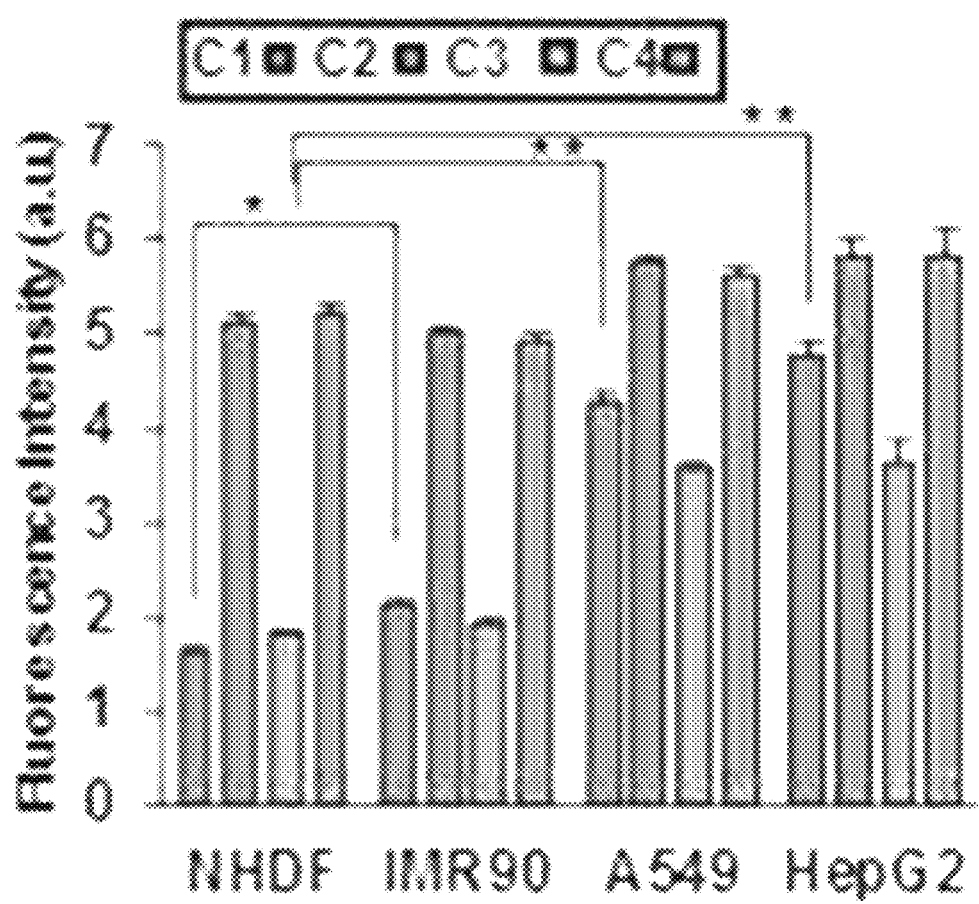

To obtain further insights into the structural and interaction features associated with the putative interactions of C1 and C3 within the carboxylesterase active side, docking and molecular dynamics (MD) simulations were carried out (FIG. 2D and FIG. 9D). After docking and further MD simulations, the binding free energy of C1 to carboxylesterase1 (CE1) was calculated to be −60.22 kcal/mol (FIG. 13). In the binding site of CE1, there are five residues (K92, A93, L96, L304, and M364) that play an important role. They contribute −1.59, −2.16, −1.56, −2.20, and −3.55 kcal/mol to the binding energetics, respectively. The binding free energy of C3 to CE1, −53.41 kcal/mol, was found to be slightly lower than that of C1. However, the residues in the binding site of CE1 that interact with C3 were found to be different from those used to bind C1 (FIG. 13). The residues A93, W357, M361, S365, Y366, P367, and M459 play a crucial role in the binding of C3 to CE1, each contributing to −1.44, −1.70, −3.87, −3.15, −3.24, −2.62, and −1.54 kcal/mol, respectively. In addition, residues D90 and K257 had repulsive interactions with C1, contributing +0.84 and +1.19 kcal/mol, respectively. These results suggest that although both C1 and C3 can fit very well into the active pocket of CE1 and are bound strongly, the specific interactions supporting enzyme substrate interactions differ in the case of these two conjugates.

Validation of Mitochondrial Targeting and Carboxylesterase-Dependent Cytotoxicity of C1

Figure 3A:
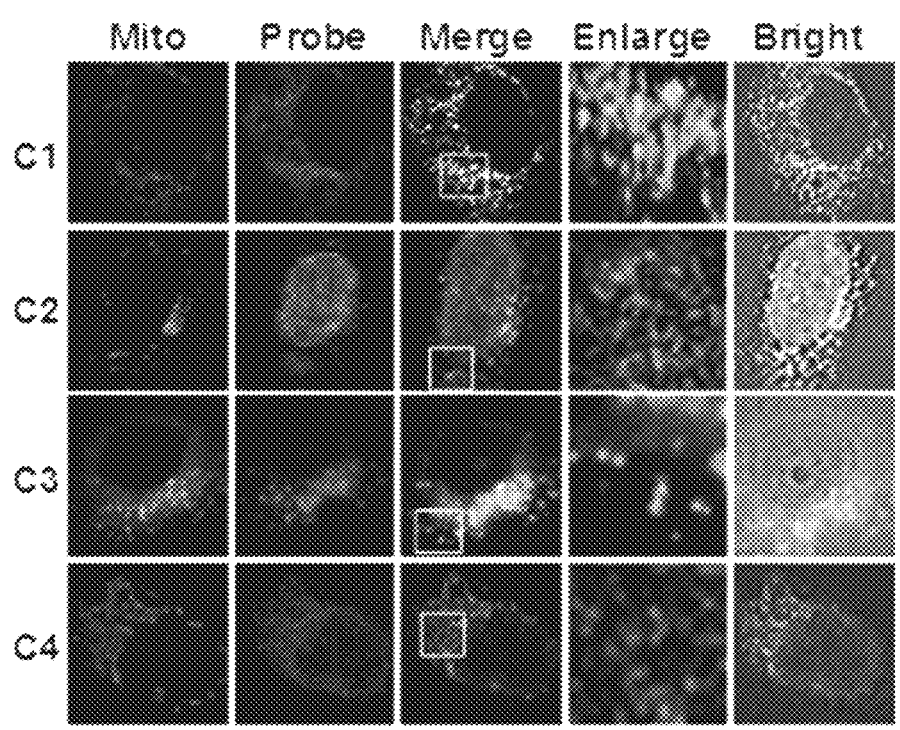
FIG. 3A shows confocal microscopy analysis of intracellular localization of compounds C1-C$_4$. HepG2 cells treated with each compound (5 μM, 24 hr) were co-stained with the mitochondrial marker MitoTracker (green). Boxed regions show co-localization of the test compounds and probe within the mitochondria.

To explore whether compounds C1 and C3 induce a cytotoxic response in cancer cells, the tumor cell selectivity of the compounds, as well as their ability to target mitochondria, in various cancer cell lines was first compared. Fluorescence image analyses revealed that C1 and C3, which contain the mitochondria-targeting lipophilic TPP moiety, were found to be taken up specifically by cancer cells (A549 and HepG2) but not by normal cells (NHDF and IMR90). In contrast, the control systems C2 and C4, which do not incorporate a TPP moiety, exhibited no cellular selectivity (FIG. 13). Further analyses using immunofluorescence in conjunction with MitoTracker as a dye revealed that C1 and C3 were located predominantly within the mitochondria for at least 24 hr after treatment, whereas C2 and C4 were distributed throughout the cell with no detectable mitochondrial localization (FIG. 3A). These findings provide support for the conclusion that the TPP moiety promotes mitochondrial targeting in the case of conjugates C1 and C3.

Figure 3B:
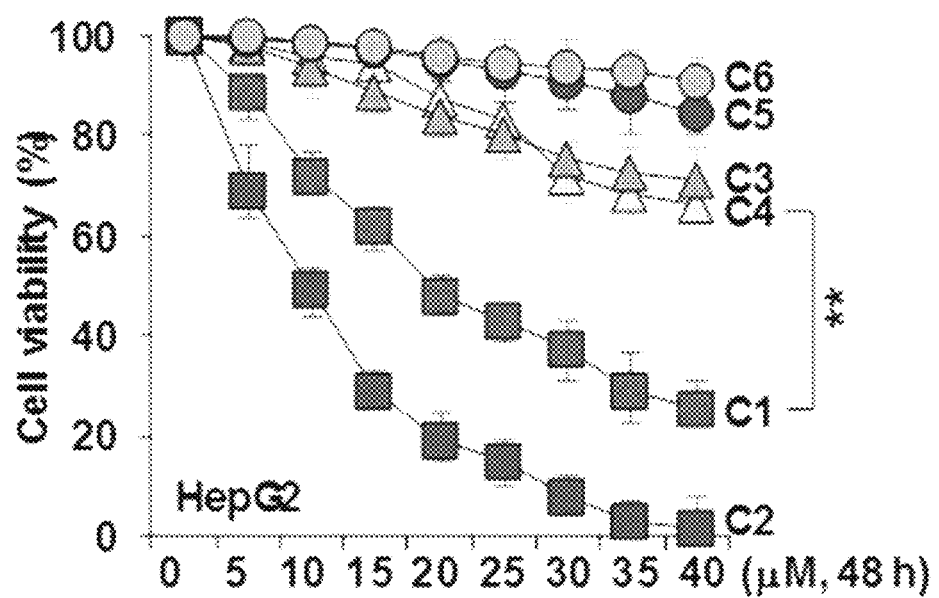
FIG. 3B shows a WST cell viability assay of compound cytotoxicity. Experiments were carried out in triplicate and the data shown represent means±SD. $p<0.01$.
Figure 10A:
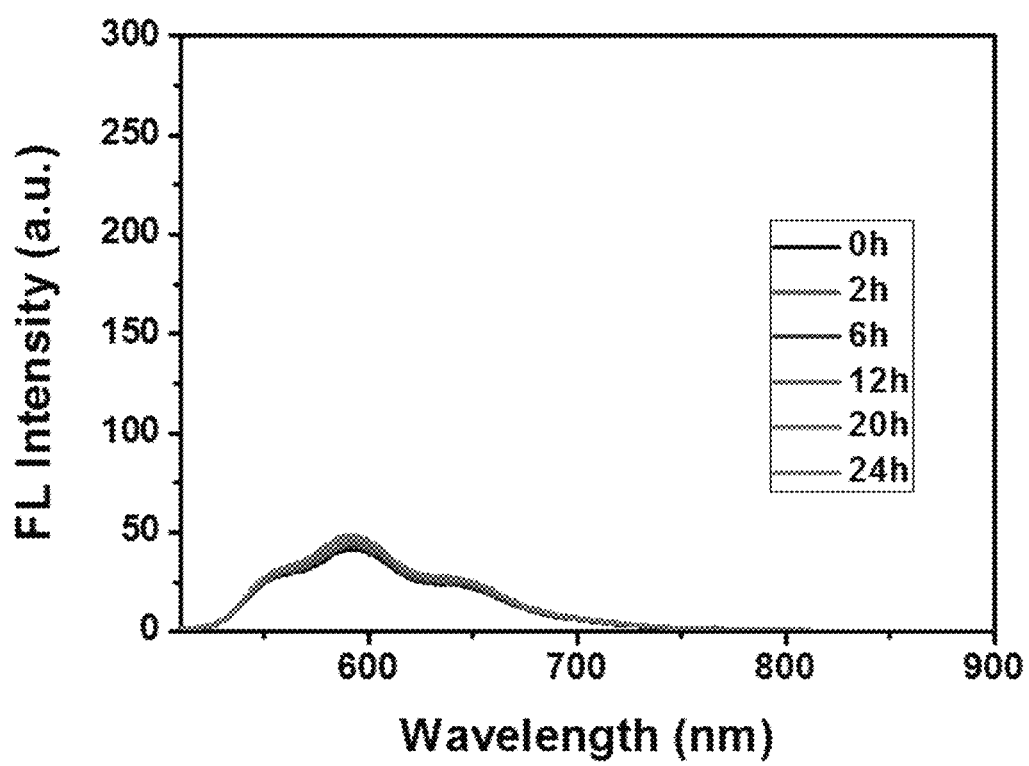
FIG. 10A shows fluorescence spectra of C3 (5 μM) recorded at different time intervals following incubation in PBS at 37° C.
Figure 10B:
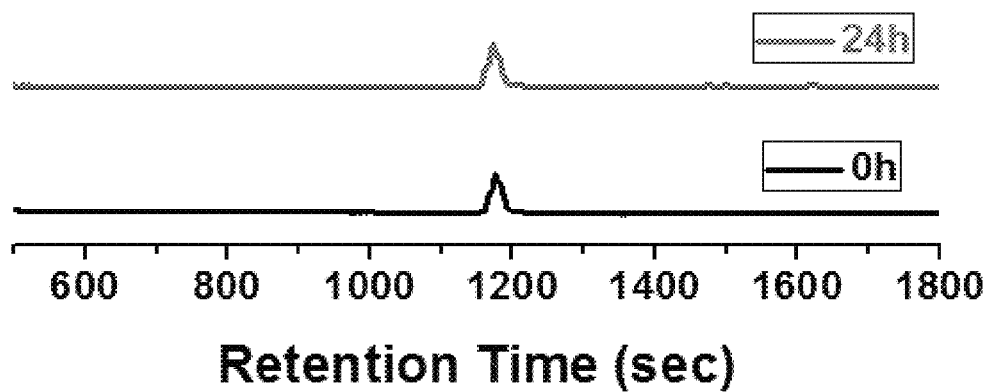
FIG. 10B shows reverse-HPLC curves of C3 (5 μM) as measured 0 and 24 h after incubation in PBS at 37° C.
Figure 11:
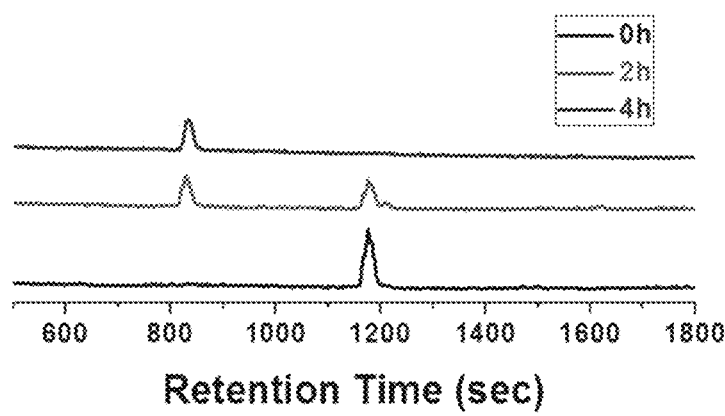
FIG. 11 shows RP-HPLC curves of C3 (5 μM) treated with carboxylesterase (1 U/mL) at 37° C. for 4 h.
Figure 12:
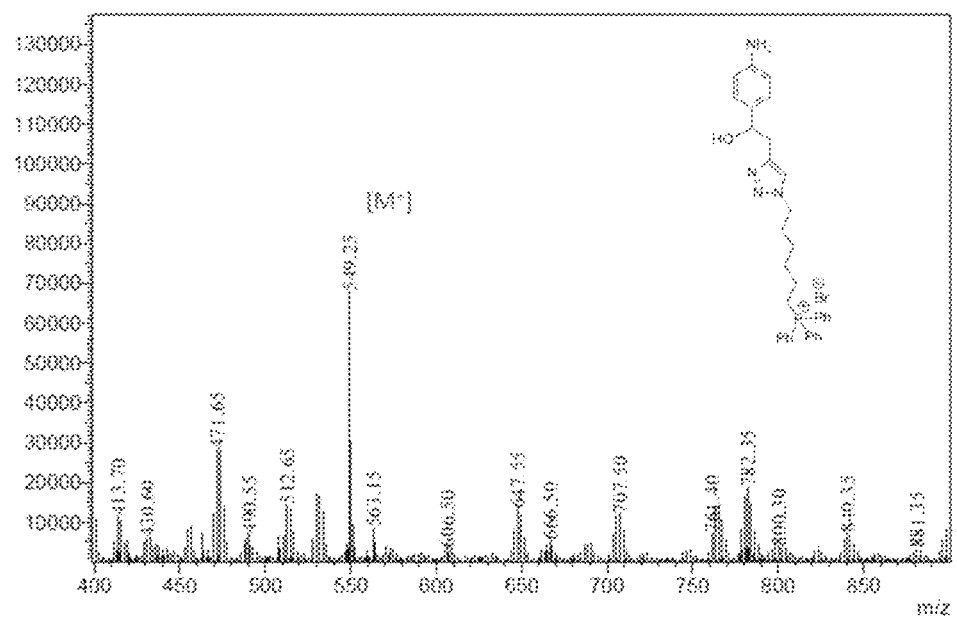
FIG. 12 is a mass spectrum of the intermediate formed upon reaction of C3 (5 μM) with carboxylesterase (1 U/mL) at 37° C. for 4 h.
Figure 15A:
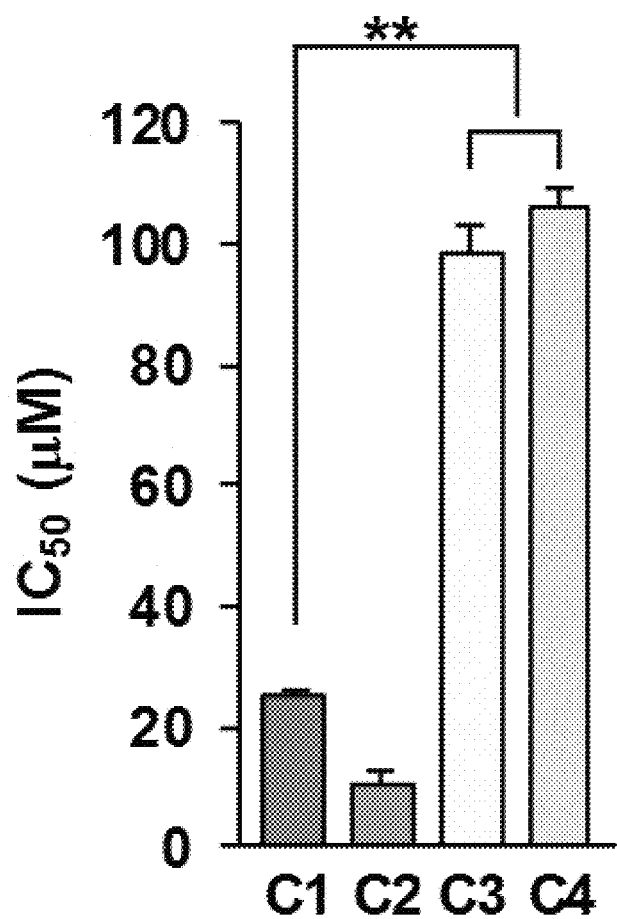
FIG. 15A shows IC$_{50}$ values of compounds in HepG2 cells and FIG. 15B shows an immunoblot assay of cleaved caspase-3 and PARP levels for the indicated compounds in HepG2 cells.
Figure 15B:
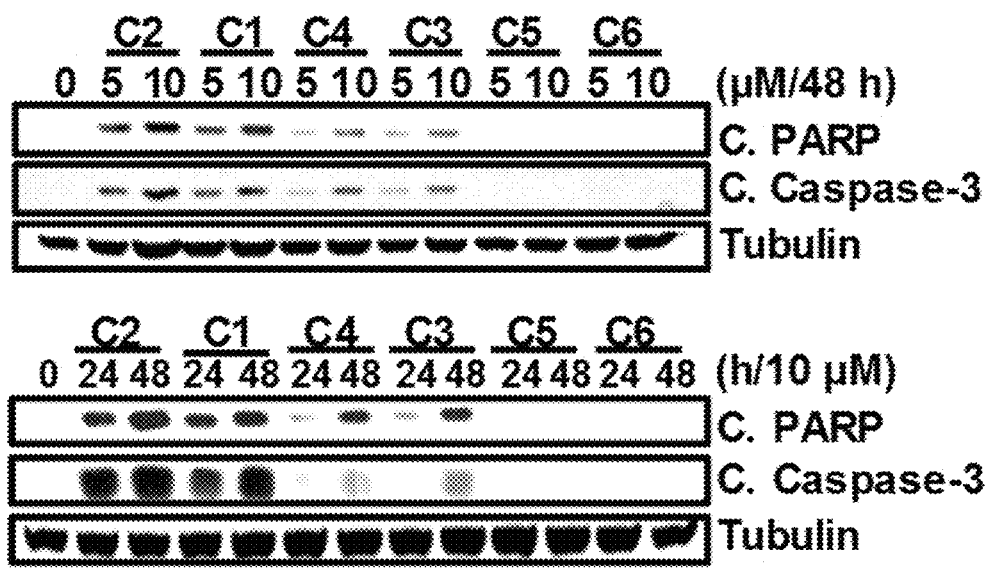

Next, the cytotoxicity of conjugates C1-C6 by using cell-survival assays was evaluated. On the basis of these studies, it was concluded that C1 and C2 induce greater cell death in a dose-dependent manner than either C3 or C4 (which lack the DCA and TPP moieties, respectively) or controls C5 and C6 (which lack the Dox subunit) (FIG. 3B). The $IC_{50}$ values of C1 and C2 were 22.1±0.325 and 10.6±1.03 µM, respectively (FIG. 10A). An immunoblot assay of cleaved caspase-3 and PARP-1 revealed that C1 has greater apoptosis-inducing activity than C2 but induces apoptosis at a later time than C2 (FIG. 15B).

Figure 3C:
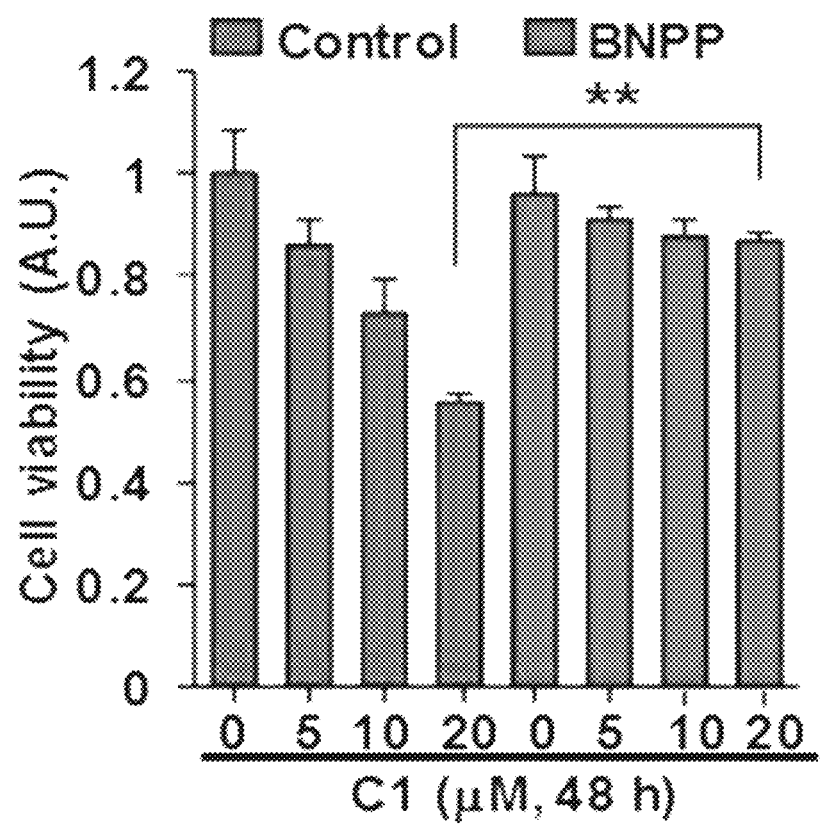
FIG. 3C shows the attenuation of C1 cytotoxic effect by BNPP. HepG2 cells were incubated with BNPP (100 μM) for 2 hr prior to C1 treatment. $p<0.01$.
Figure 3D:
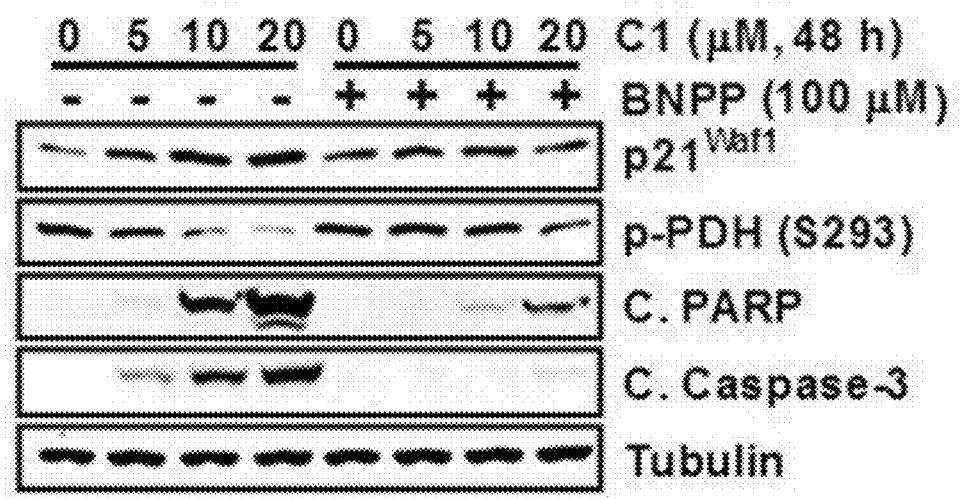
FIG. 3D shows an immunoblot assay showing the effect of C1 on p21$^{Waf1}$ and phosphorylated PDH (p-PDH) levels and its blocking by BNPP pretreatment. Cleaved caspase-3 and PARP-1 levels were examined to assess apoptosis induction. C, cleaved.
Figure 3E:
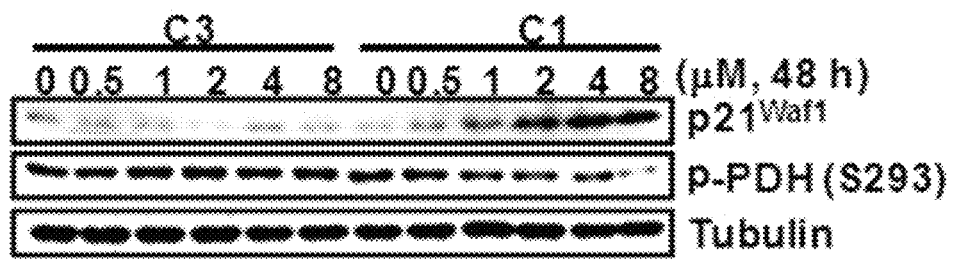
FIG. 3E shows an immunoblot assay for comparison of the effect of C1 and C3 on p21$^{Waf1}$ and p-PDH levels.

To understand the role of the carboxylesterase in the release of DCA and Dox, the effect of the known carboxylesterase inhibitor, bis-(4-nitrophenyl)phosphate (BNPP), on the cytotoxicity of C1 was tested. BNPP pretreatment strongly attenuated the C1-driven decrease in cell viability, as well the dose-dependent induction of apoptosis (FIG. 3C). Moreover, C1 treatment led to up- and downregulation of $p21^{Waf1}$ and phosphorylated PDH levels, which are mediated by Dox and DCA, respectively. Moreover, these effects of C1 were strongly inhibited by pretreatment with BNPP (FIG. 3C and FIG. 3D). Unlike C1, conjugate C3, which lacks a DCA subunit, showed no effect on $p21^{Waf1}$ or PDH phosphorylation (FIG. 3E). Together, these results provide support for the suggestion that the concurrent presence of the three elements (DCA, Dox, and TPP) in C1 allows for synergistic PDK inhibition in combination with Dox drug release in human cancer cells.

Cytotoxic Effect of C1 on Drug-Resistant Tumor Cells

Figure 4A:
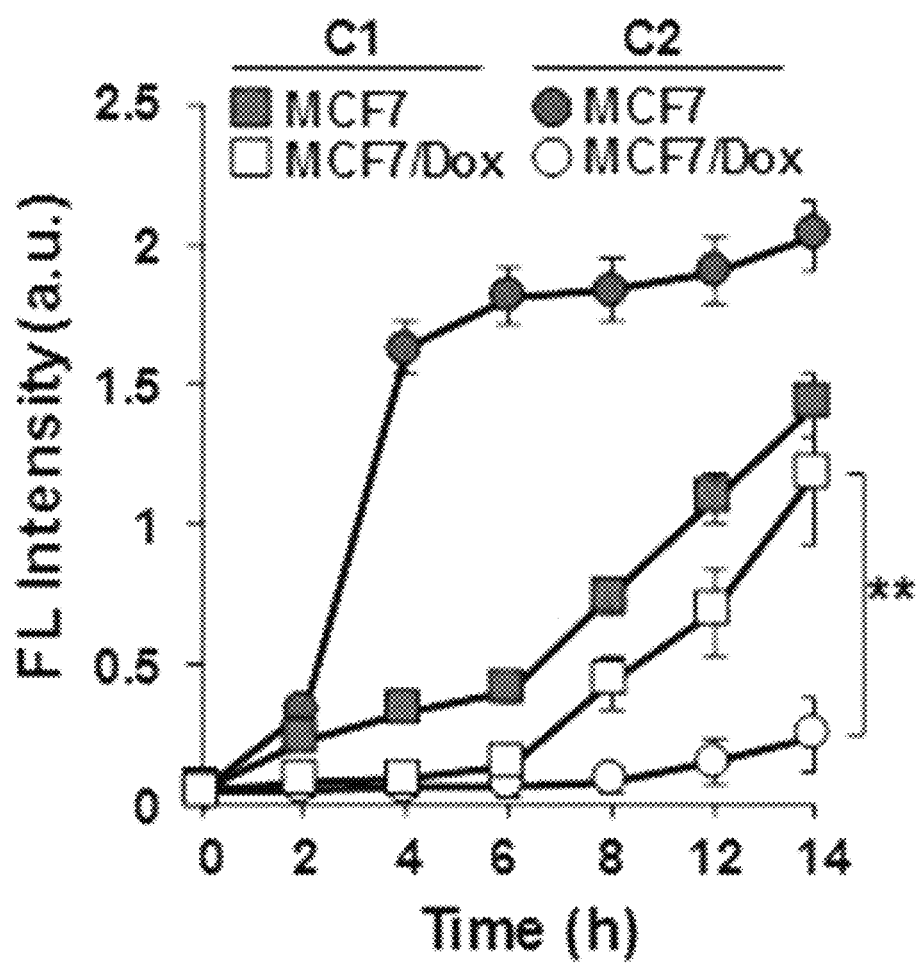
FIG. 4A shows the comparison of intracellular levels of C1 and C2 in MCF7 and MCF7/Dox cells. Fluorescence intensities were measured with SpectraMAX 13. Data represent means±SD. $p<0.01$.
Figure 16A:
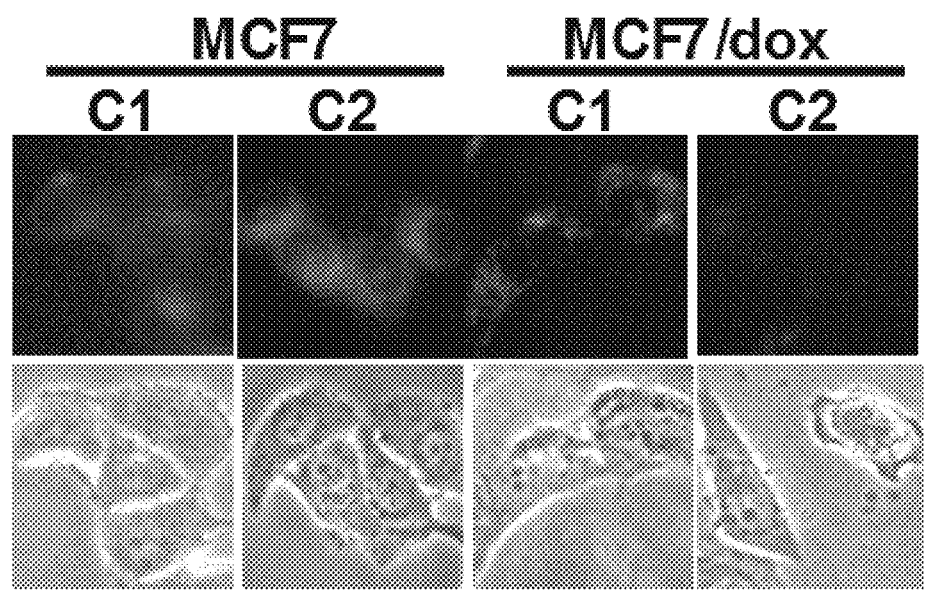
FIG. 16A shows fluorescence microscope images showing the intracellular accumulation of C1 and C2 in MCF7 and MCF7/Dox resistant cells and FIG. 16B shows mitochondrial localization of C1 in MCF7 and MCF7/Dox cells. Mito-tracker (green) was utilized to show the mitochondria.
Figure 16B:
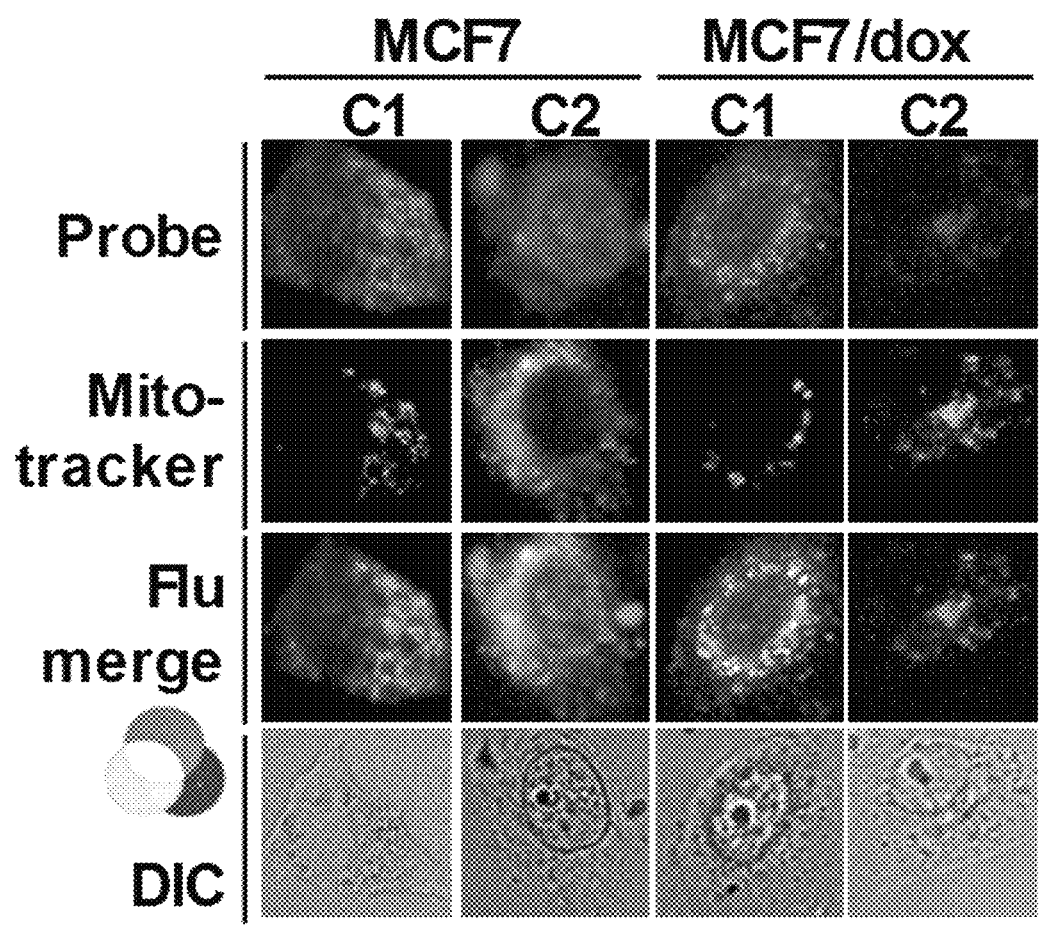
Figure 17A:
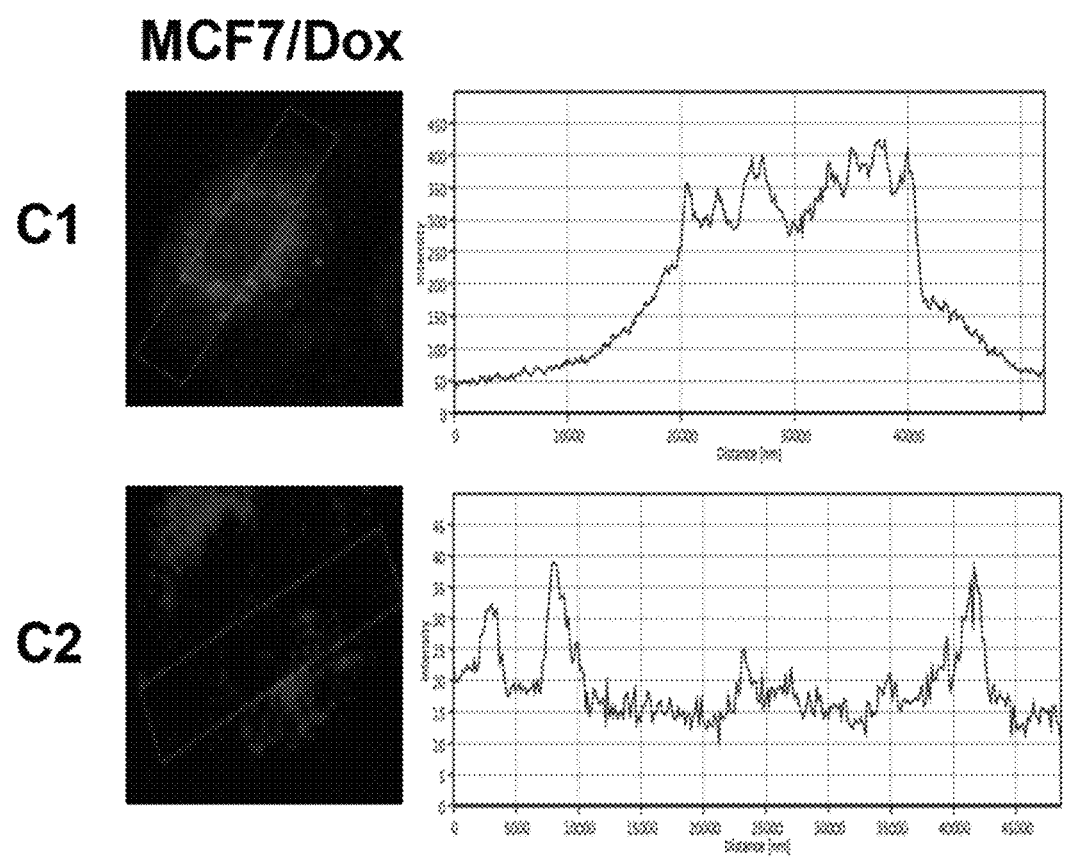
FIG. 17A shows confocal microscopy images showing intracellular florescence of C1 and C2. Quantitative analysis of the fluorescence intensity was made using the LSM700 software.
Figure 17B:
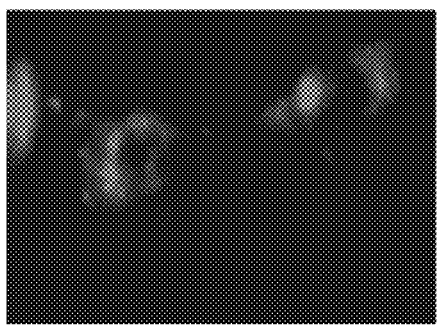
FIG. 17B shows C1 and C2 staining images in NCI-Dox cells.
Figure 17B:
Figure 17B:
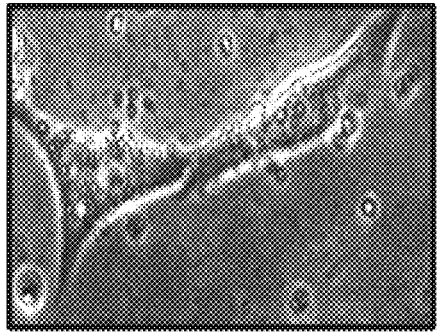
Figure 17B:
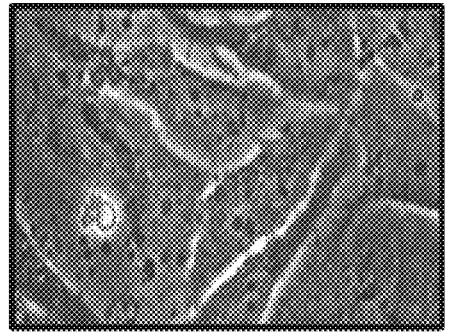

To assess whether DCA-based PDK inhibition and Dox release overcome the MDR property of tumor cells, the effect of the inventive conjugates on the breast cancer cell line MCF7 and its Dox-resistant subline MCF7/Dox was compared. The latter cell line is characterized by an enhanced drug efflux capability. A fluorescence assay revealed that C2 (an analog of C1 that lacks the TPP targeting subunit) was accumulated at a substantially lower level in MCF7/Dox than in MCF7 (FIG. 16A). In contrast, C1 accumulated at a comparable level in both MCF7 and MCF7/Dox cells for up to 12 hr after treatment (FIG. 4A). Immunoblotting studies revealed that C1, but not C2, exhibited mitochondrial localization in both MCF7 and MCF7/Dox cells (FIG. 16B). Similar results were obtained in another MDR tumor cell line, NCI/Dox (FIGS. 17A and 17B).

Figure 4B:
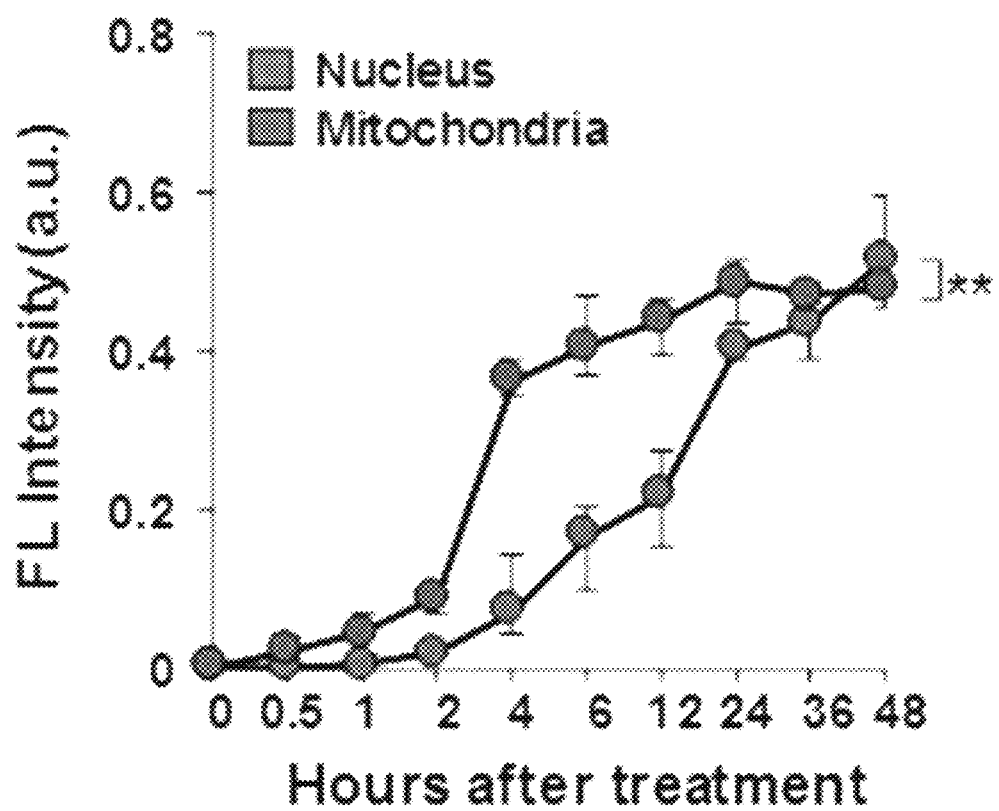
FIG. 4B shows a cell fractionation assay showing the mitochondria-to-nucleus trafficking of C1. Data represent means±SD. $p<0.05$.

In order to evaluate more precisely the subcellular localization of C1, a cell fractionation assay was performed. On this basis, it was concluded that after treatment, C1 localizes initially to the mitochondria. After enzymatic cleavage of DCA and release of free Dox, the Dox then translocates to the nucleus over the course of approximately 2 hr (FIG. 4B). This ability to localize to the nucleus is considered particularly beneficial for an agent, such as Dox, which is thought to mediate its antitumor action within the nucleus. Mitochondrial targeting of Dox and other nuclei-dependent drugs has been reported. However, the subsequent time-dependent nuclear translocation behavior seen after administration of C1 to MDR cancer cells is without precedent.

Figure 4C:
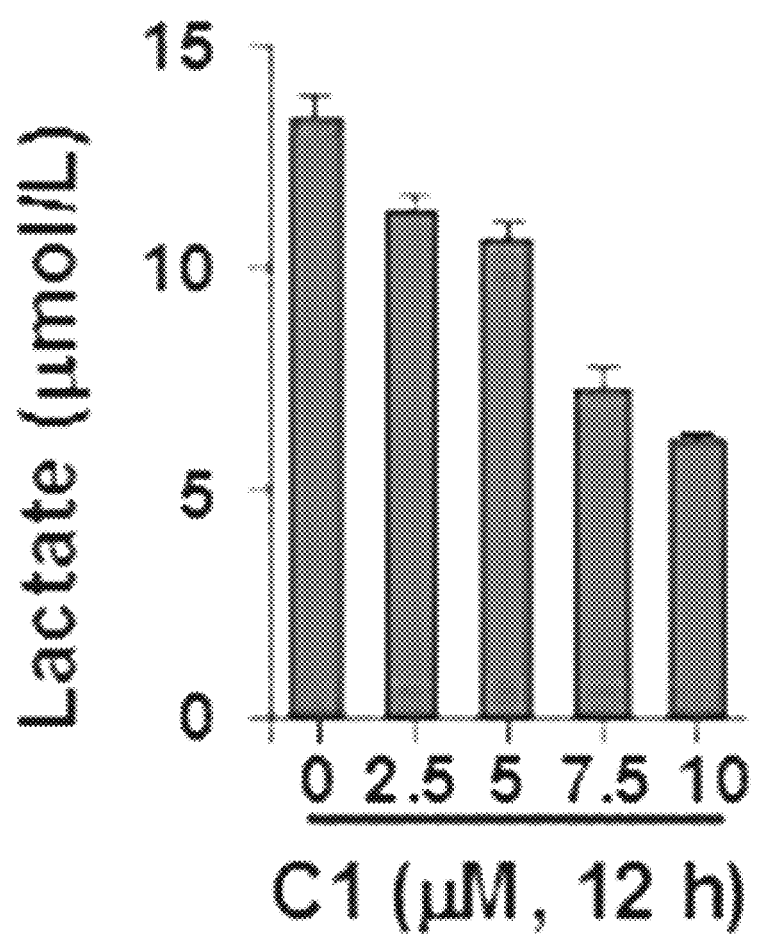
FIG. 4C shows the dose-associated effect of C1 on intracellular lactate accumulation. Data represent the mean±SD (n=3 experimental replicates). *$p<0.05$, **$p<0.01$.
Figure 18A:
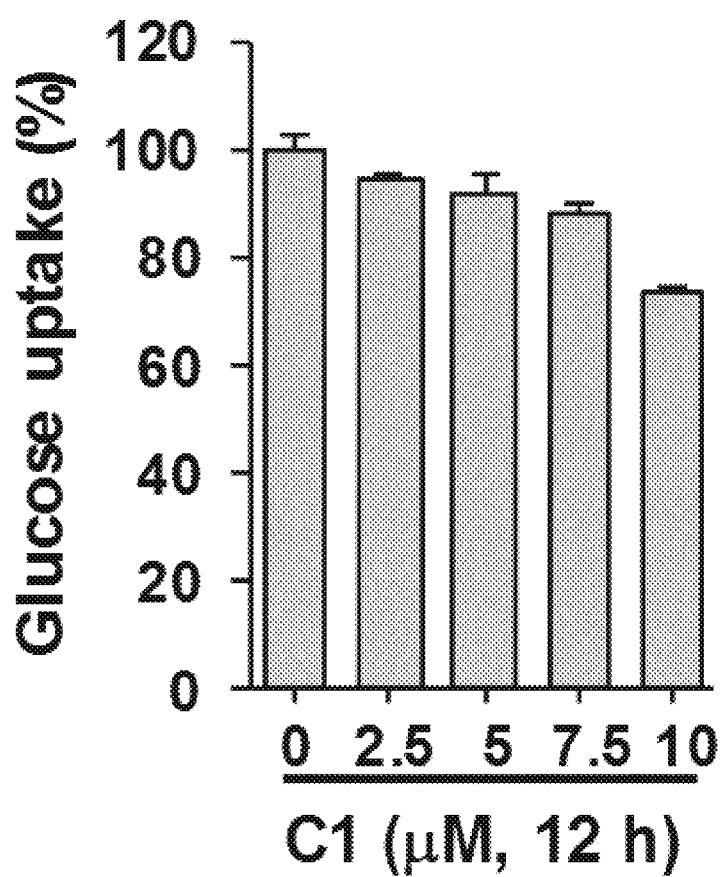
FIG. 18A shows dose-associated effect of C1 on glucose uptake and FIG. 18B shows intracellular ATP levels in MCF7/Dox cells (mean±SD, n=3, * $p<0.05$)
Figure 18B:
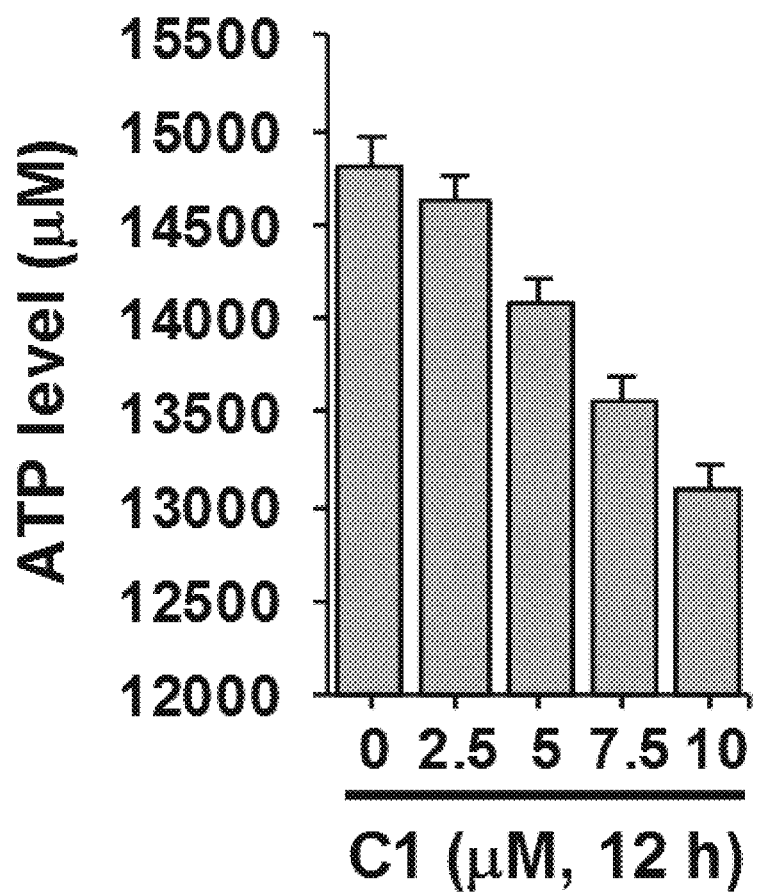

To address whether carboxylesterase-mediated DCA release blocks aerobic glycolysis and thus drives apoptosis in the case of the drug-resistant cells, the effect of C1 on lactate accumulation was tested. Treatment of MCF7/Dox cells with C1 led to a dose-dependent reduction of intracellular lactate levels (FIG. 4C). This was accompanied by decreased glucose uptake and lowered intracellular ATP levels (FIGS. 18A and 18B). These results are consistent with the hypothesis that compound C1 would trigger mitochondrial dysfunction by releasing DCA and modulating the pyruvate metabolic pathway in these cancer cells.

Figure 4D:
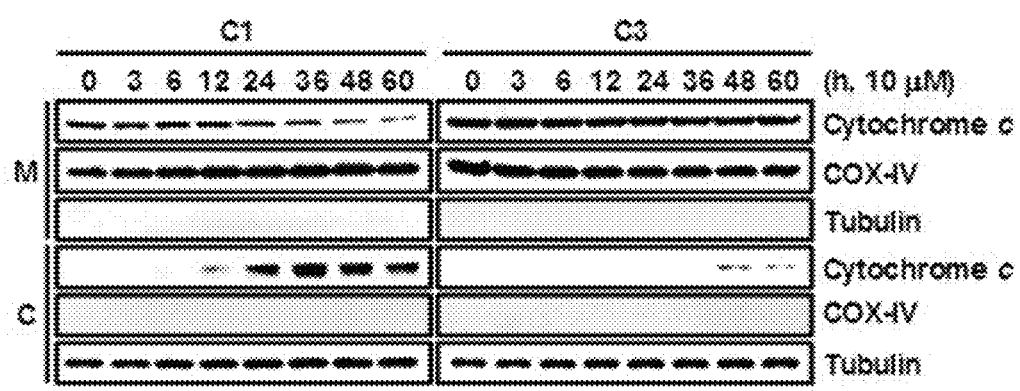
FIG. 4D shows an immunoblot assay showing the C1-induced release of cytochrome c from the mitochondria. MCF7/Dox cells were treated with C1 or C3 as indicated, and the cytosolic (C) and mitochondrial (M) fractions were subjected to immunoblot assay. COX-IV and tubulin were used as markers for the mitochondria and cytosol fractions, respectively.
Figure 4E:
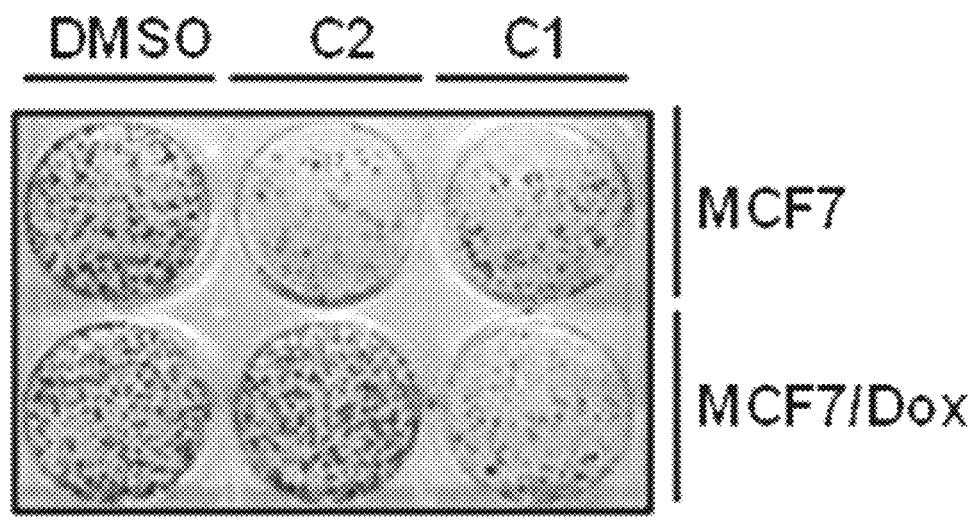
FIG. 4E shows the suppression of colony-forming ability of MCF7/Dox cells induced by C1 but not C2.
Figure 19A:
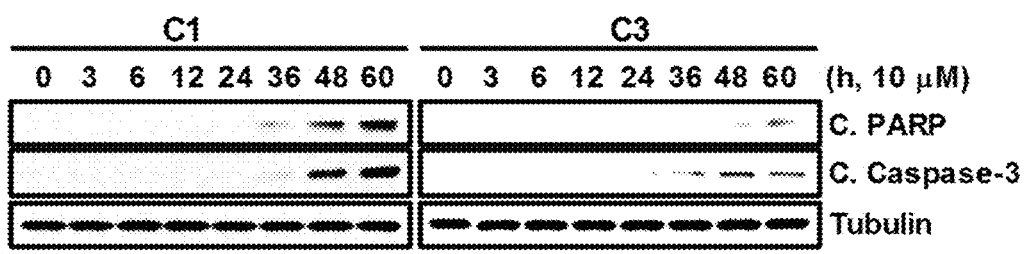
FIG. 19A shows dose dependent effect of Dox+DCA and C1 on cleaved PARP levels in the MCF7/Dox cells.

The crucial role of carboxylesterase-mediated drug release was further supported by the observation that C1 induces cytochrome c release from the mitochondria, cleavage of caspase-3 and PARP-1, and a decrease in cell viability; in contrast, C3, which does not provide for PDK inhibition, fails to evoke these effects (FIG. 4D, FIG. 19A and FIG. 19B). Moreover, C1 showed a strong inhibitory effect on the colony-forming ability of both MCF7 and MCF7/Dox cells, whereas C2 showed this effect only in the case of the MCF7 cells but not the resistant MCF7/Dox cells (FIG. 4E).

Collectively, the above results provide support for the conclusion that the presence of the TPP subunit leads to initial targeting of C1 within the mitochondria and that this helps overcome drug efflux processes that would normally serve to reduce the effective concentration of Dox within a cancer cell. These results are also consistent with the conclusion that DCA released from C1 modulates what is otherwise an aberrant mitochondrial metabolism in the case of resistant MCF7/Dox cells. A particular benefit of the inventive compound C1 is that it allows the further translocation of released Dox to the nucleus. The net result is synergistic apoptotic cell death.

C1-Induced Regression of Drug-Resistant Tumors

Figure 5A:
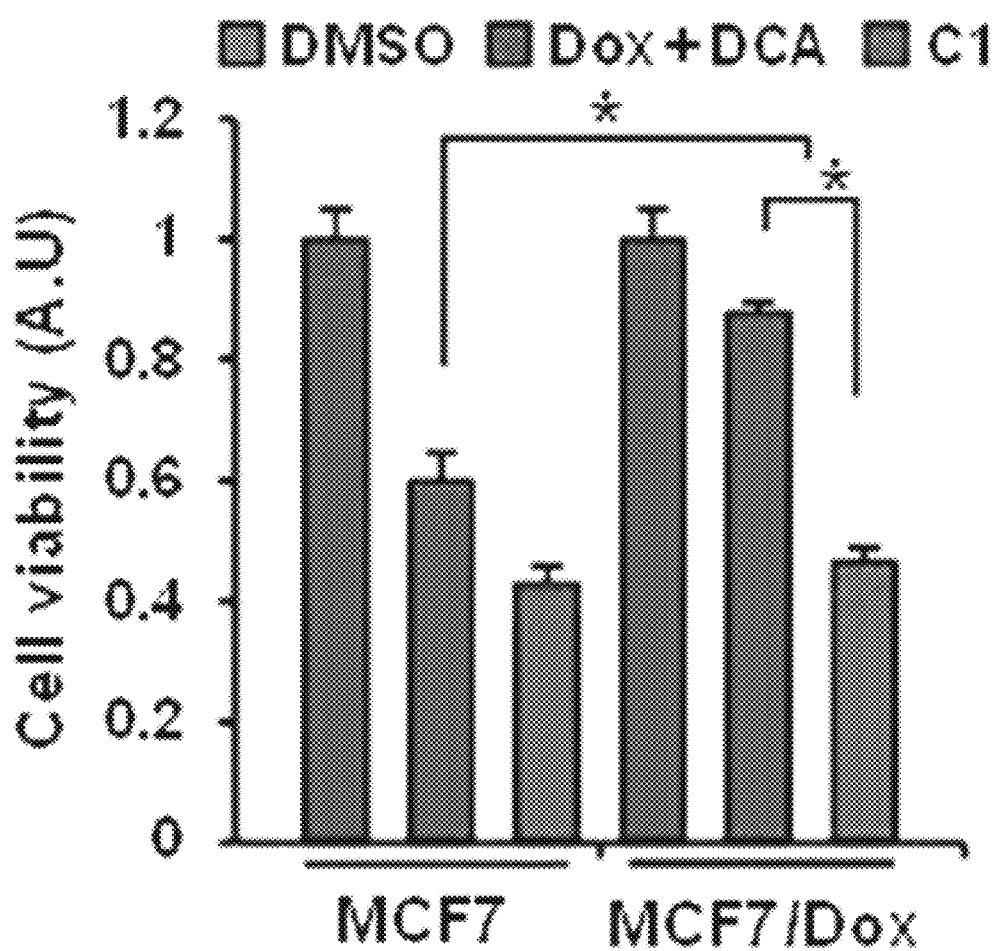
FIG. 5A shows the effect of C1 or doxorubicin combined with DCA on cell viability in MCF7 and MCF7/dox cells. Data represent the mean±SD. *$p<0.05$.
Figure 5B:
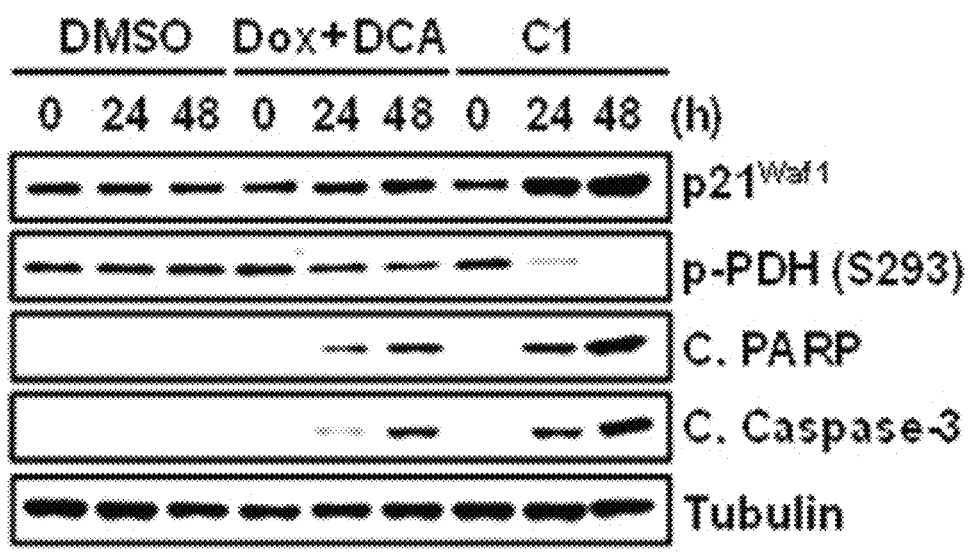
FIG. 5B shows the comparison of the efficacy of C1 versus doxorubicin combined with cleaved PARP in the MCF/Dox cells.
Figure 19C:
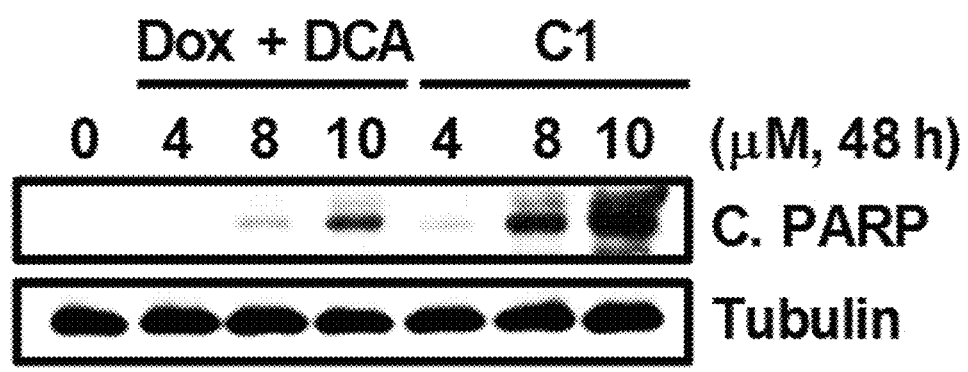
FIG. 19C shows the time-dependent effect of C1 and C3 on caspase-3 and PARP levels in the MCF/Dox cells. Apoptosis was assessed by monitoring cleaved caspase 3 (C.caspase-3) and cleaved PARP (C.PARP) protein levels.

The cytotoxic effects of C1 were also compared with those produced by an equivalent concentration of Dox and DCA (Dox+DCA). Whereas both C1 and Dox+DCA induced a comparable reduction in cell viability in the case of the MCF7 cell line, only C1 produced an appreciable cytotoxic effect in the resistant MCF7/Dox cells (FIG. 5A). Moreover, the effect of C1 was comparable in both cell lines. Treatment with C1 also led to greater levels of $p21^{Waf1}$, reduction of PDH phosphorylation, and cleavage of caspase-3 and PARP-1 than did treatment with Dox+DCA. In the case of C1, both time- and dose-dependent behavior was seen (FIG. 5B and FIG. 19C).

Figure 5C:
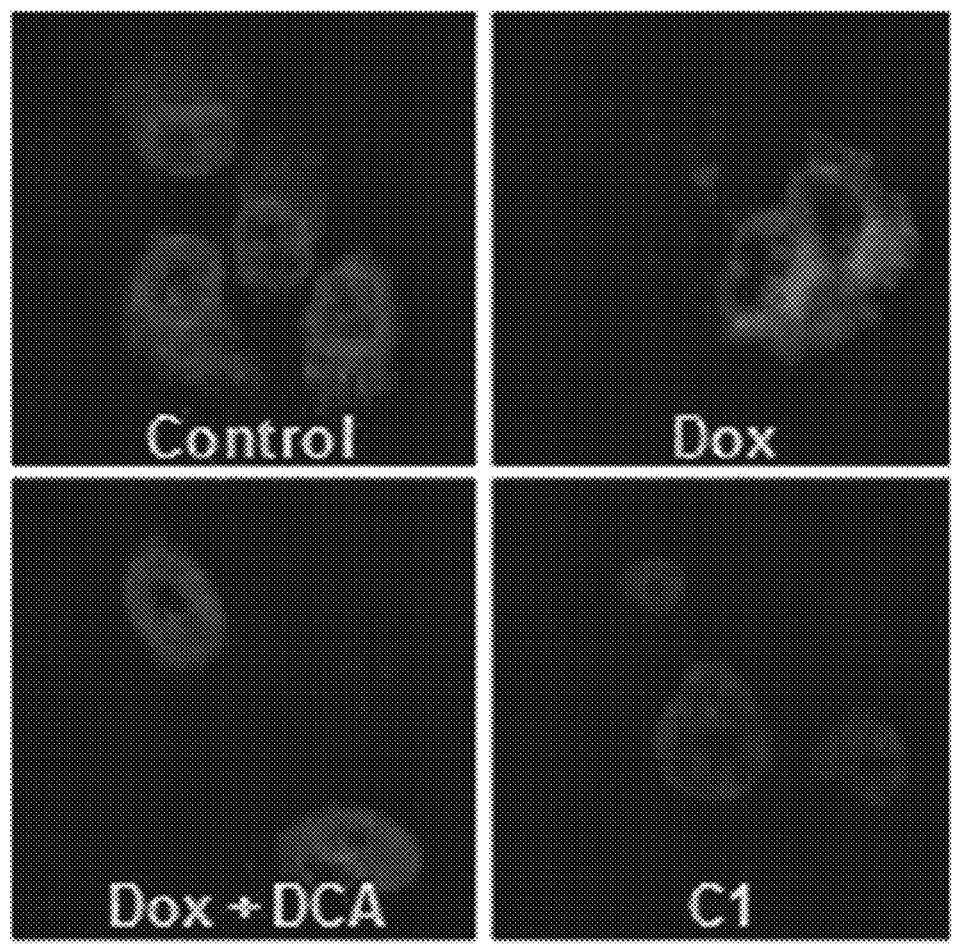
FIG. 5C shows confocal laser scanning microscope (CLSM) images showing qualitatively the mitochondrial membrane potential in MCF7/Dox cells observed upon incubation with C1, Dox+DCA, and Dox, respectively, for 48 hr with MitoView 633 (Biotium) staining for the mitochondrial (red) channel and Hoechst 33342 staining for the nucleus (blue) channel.
Figure 20:
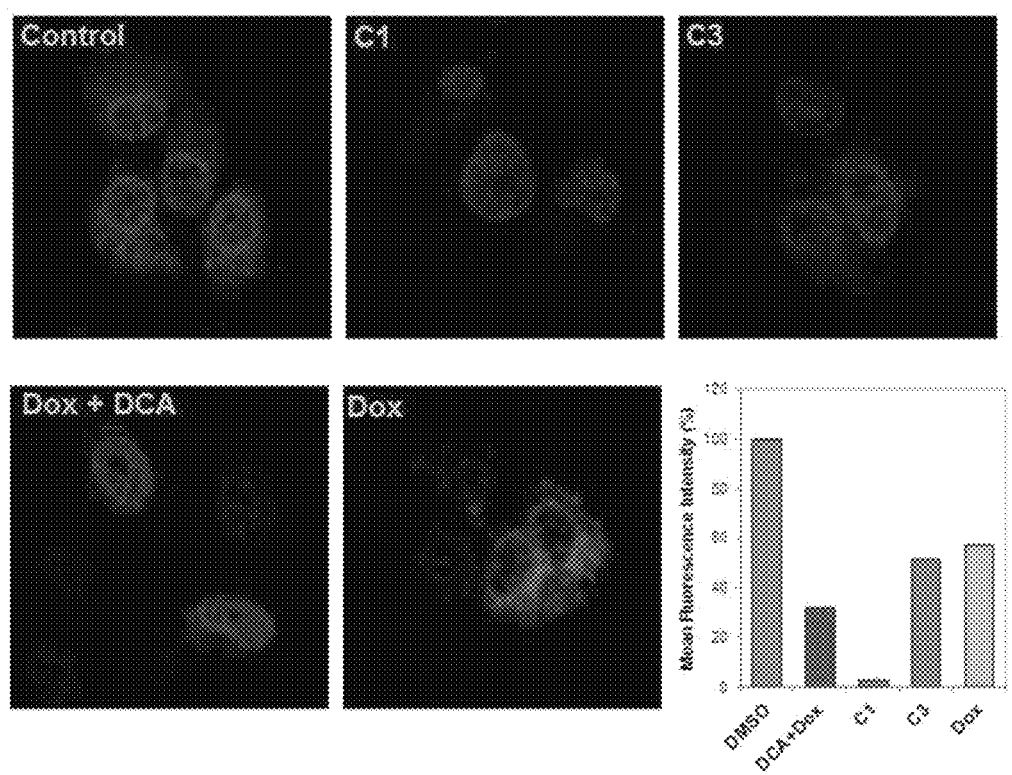
FIG. 20 shows confocal laser scanning microscope (CLSM) images and quantitative results for mitochondrial membrane potential in MCF7/Dox cells observed upon incubation with C1, C3, Dox+DCA and Dox for 48 h with MitoView™ 633 (Biotium) staining for the mitochondrial (red) channel and Hoechst 33342-staining for the (blue) nucleus channel.
Figure 21A:
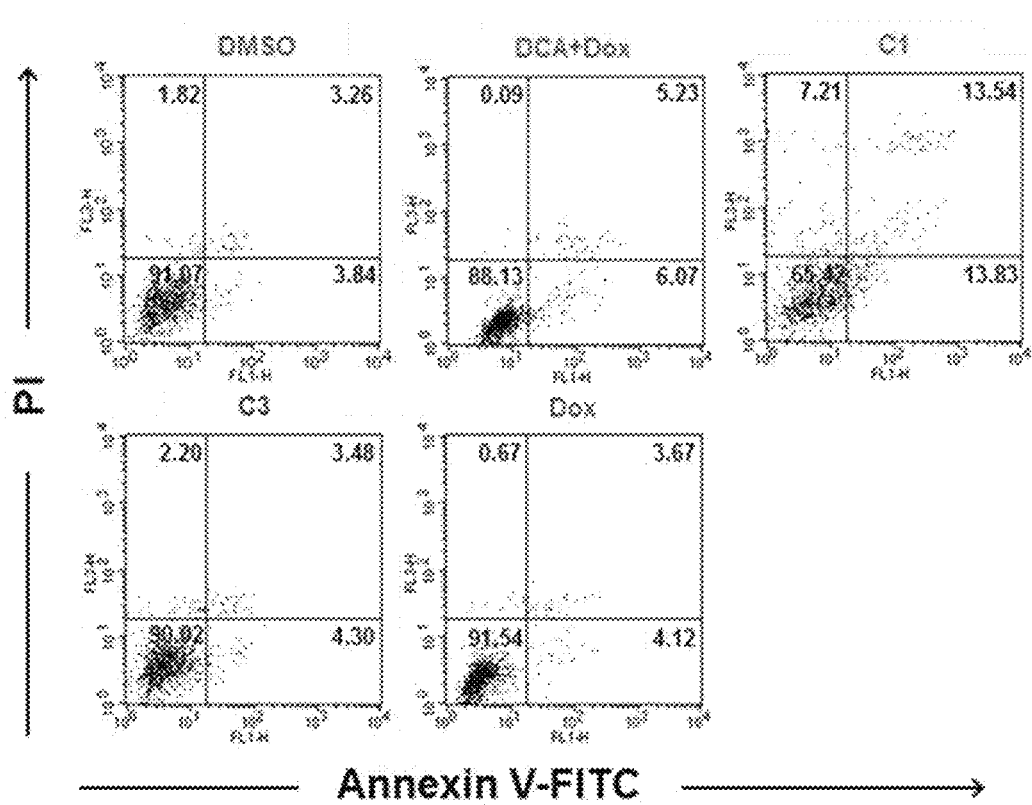
FIG. 21A shows an apoptosis assay for MCF7/Dox cells upon incubation with DMSO, C1, C3, DCA+Dox and Dox for 24 h using an Annexin V-FITC/PI detection kit.
Figure 21B:
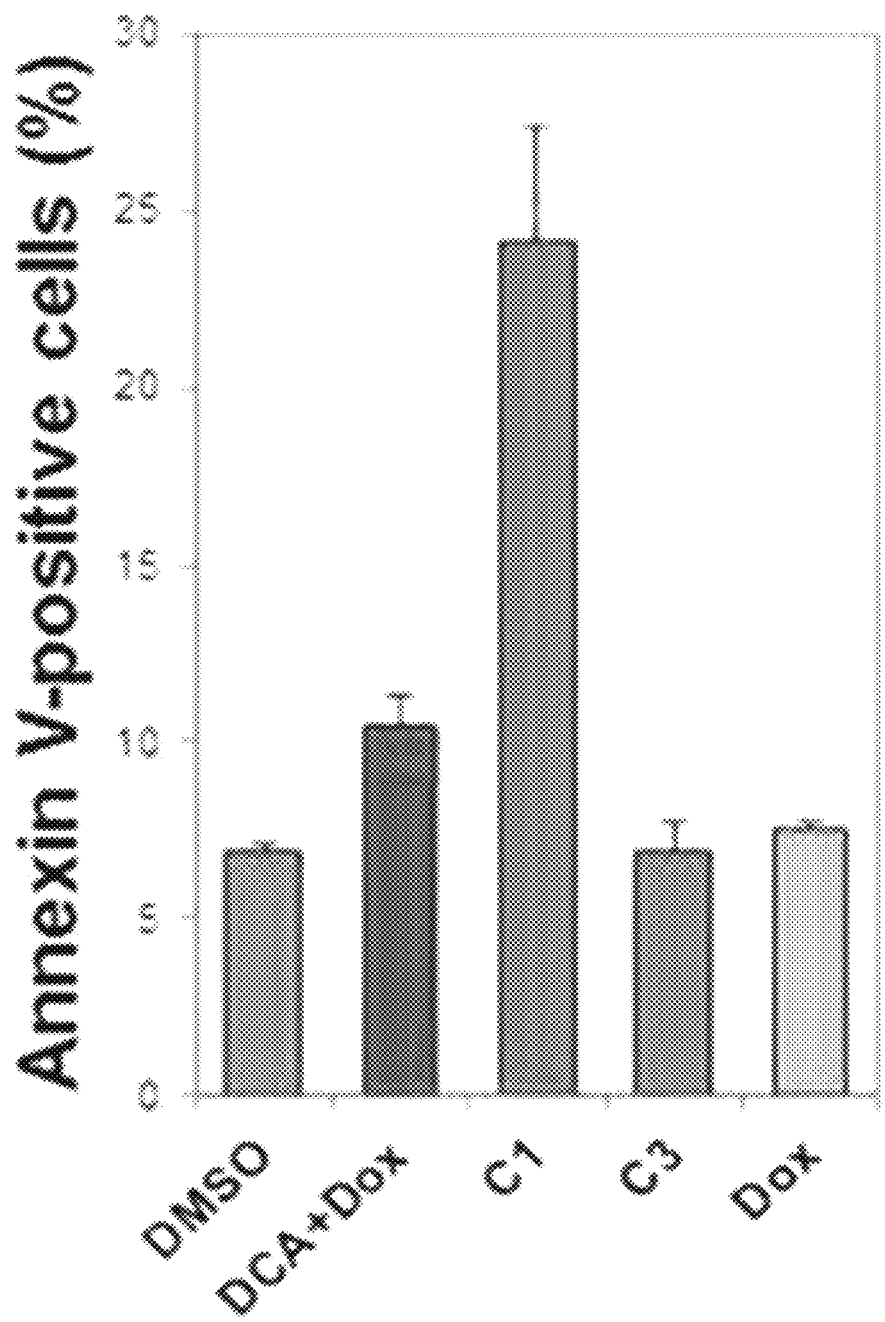
FIG. 21B shows quantitative results for cell viability in MCF7/Dox cells as observed upon treatment with C1, C3, DCA+Dox and Dox for 24 h (n=3, * p<0.005)

Confocal laser scanning microscope imaging (CLSM) of the mitochondrial membrane potential (dyr.) revealed that treatment with C1 induces a drastic decrease in $\Delta\psi_m$, (by ca. 96%) and did so more effectively than either C3, Dox, or Dox+DCA (FIG. 5C and FIG. 20). Flow cytometric analysis of Annexin V also revealed that C1 promotes both early and late apoptosis and does so more effectively than either C3, free Dox, or Dox+DCA (FIG. 21).

Figure 5D:
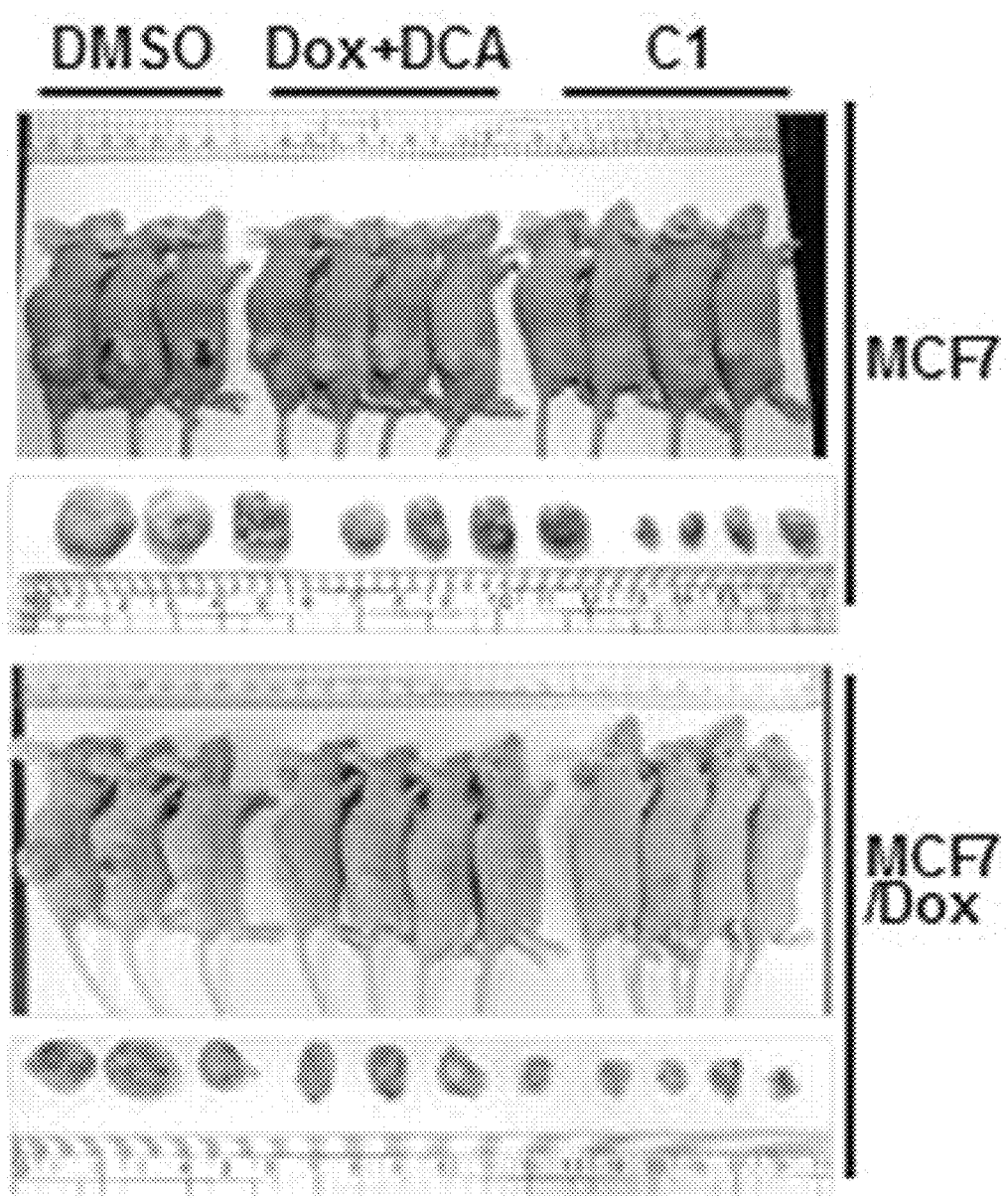
FIG. 5D shows representative images of MCF7 and MCF7/Dox xenograft tumors treated with DMSO control, Dox+DCA, and C1.
Figure 5E:
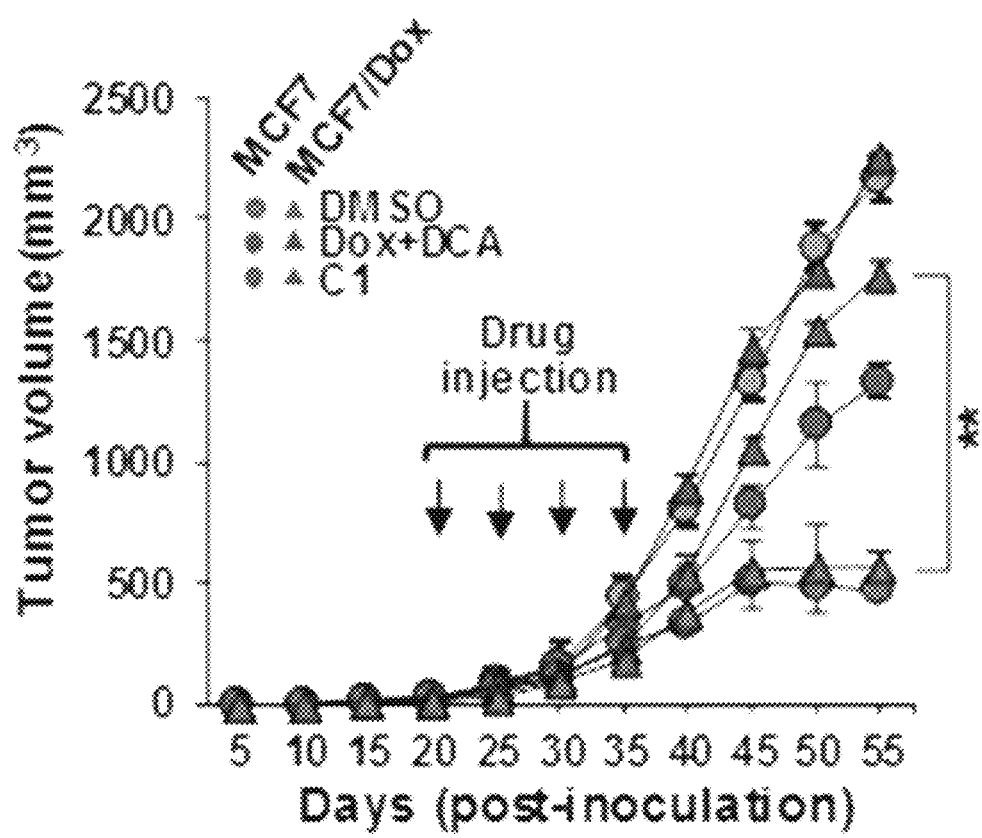
FIG. 5E shows the C1-induced regression of MCF7 and MCF7/Dox tumors (mean±SD, n=8 per group, **$p<0.01$).
Figure 5F:
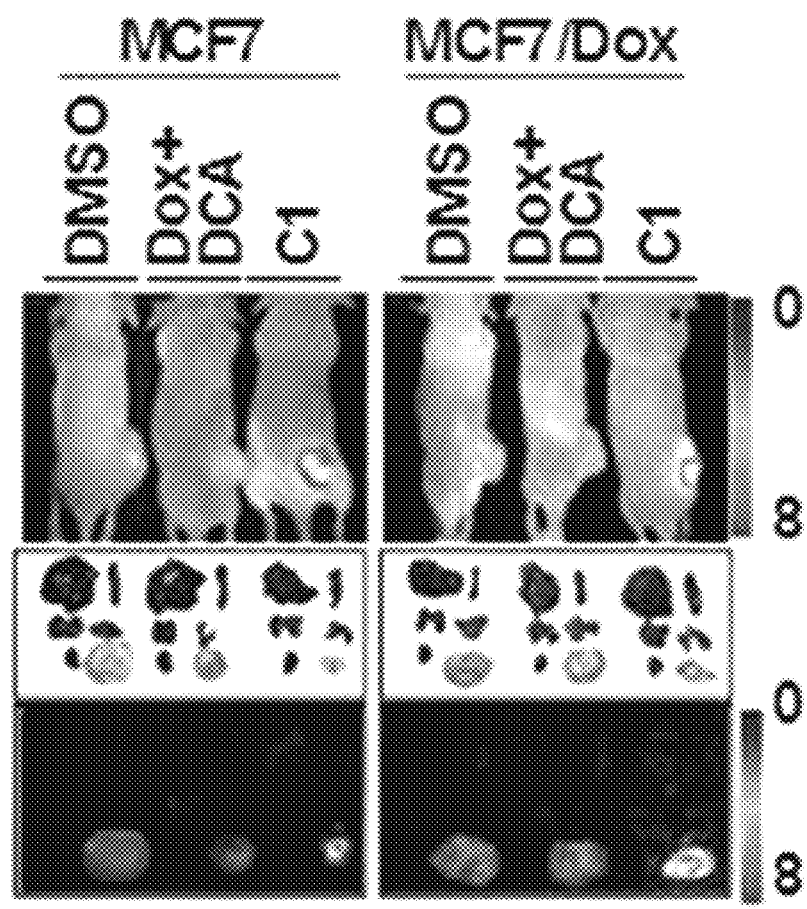
FIG. 5F shows representative fluorescence images of mice bearing MCF7 and MCF7/Dox tumors and ex vivo images of dissected organs.
Figure 22A:
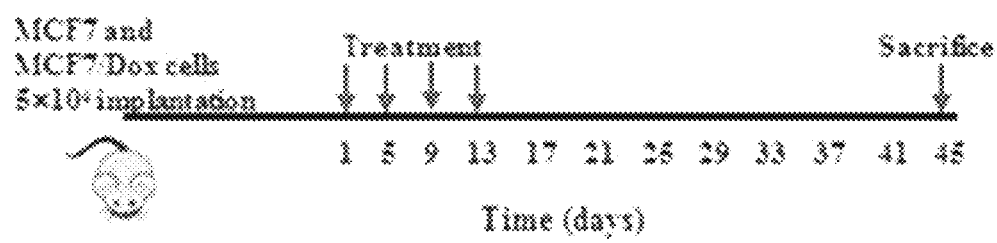
FIG. 22A shows Western blot analysis of apoptosis markers in MCF7/Dox cells treated with C1 or doxorubicin combined with DCA.
Figure 22B:
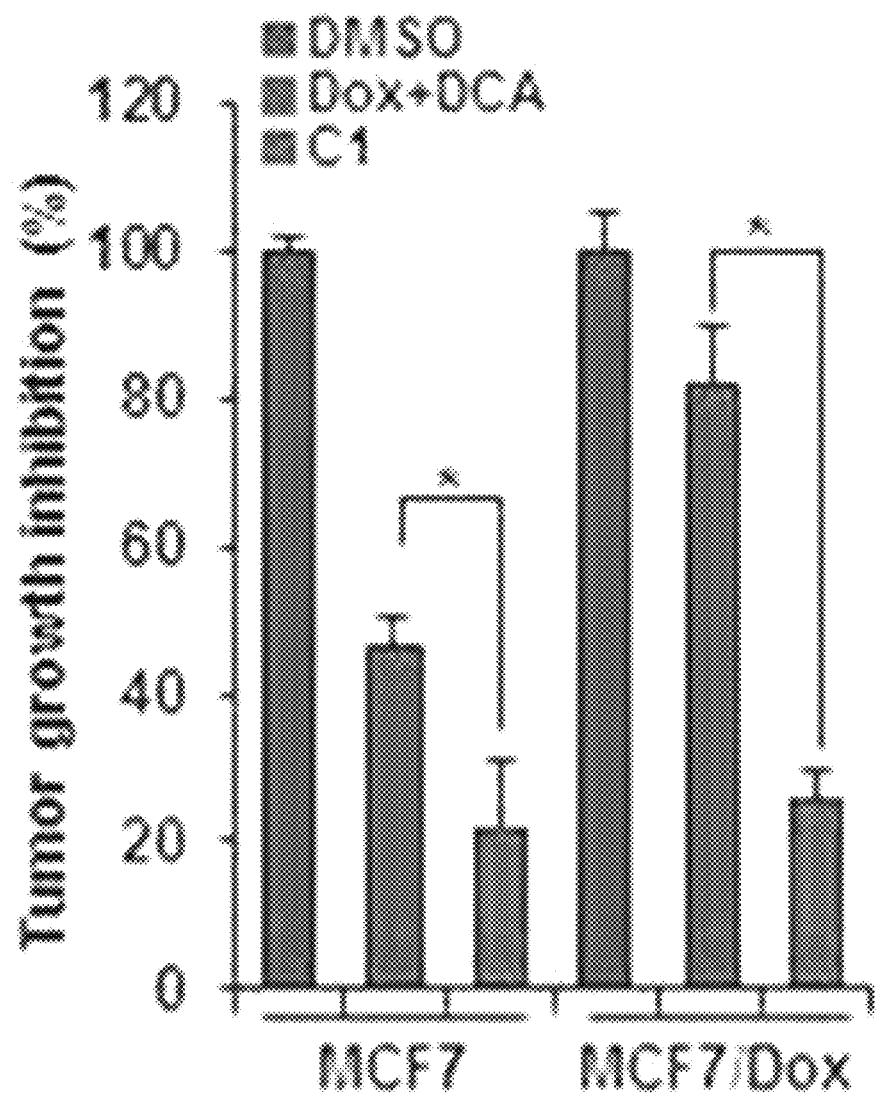
FIG. 22B shows tumor growth inhibition after treatment with Dox combined with DCA, C1, and DMSO over 50 d (mean±SD, n=8)
Figure 22C:
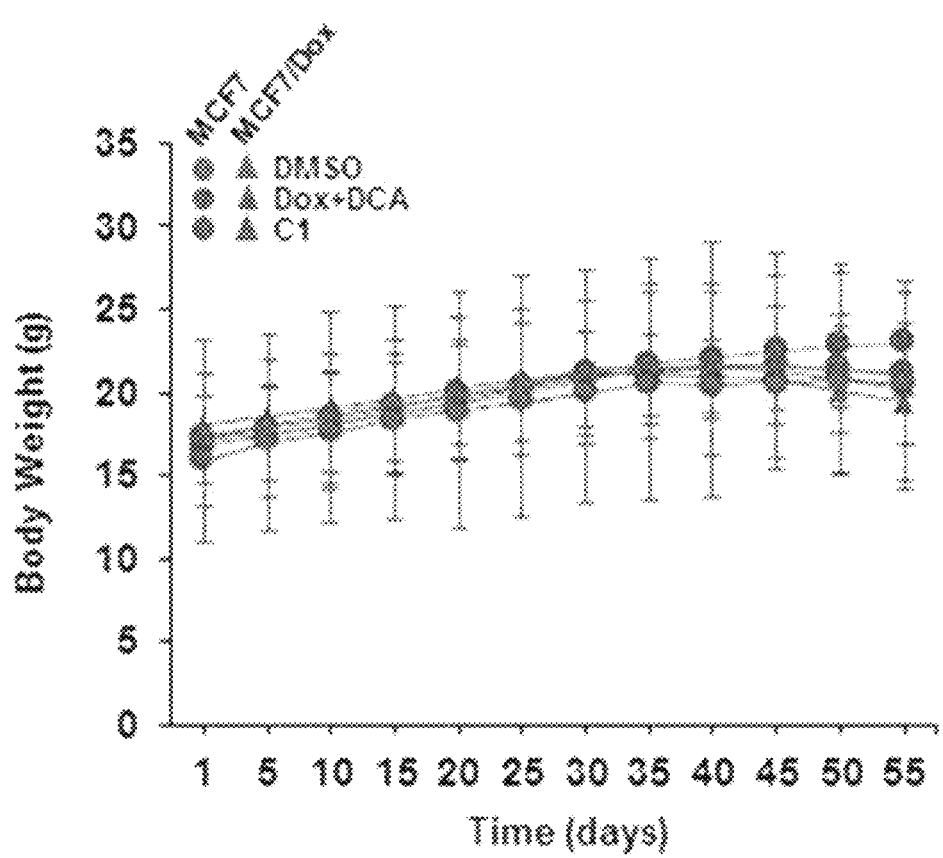
FIG. 22C shows body weight changes of nude mice bearing MCF7/Dox tumors observed upon treatment with DMSO, Dox+DCA, and C1.
Figure 23A:
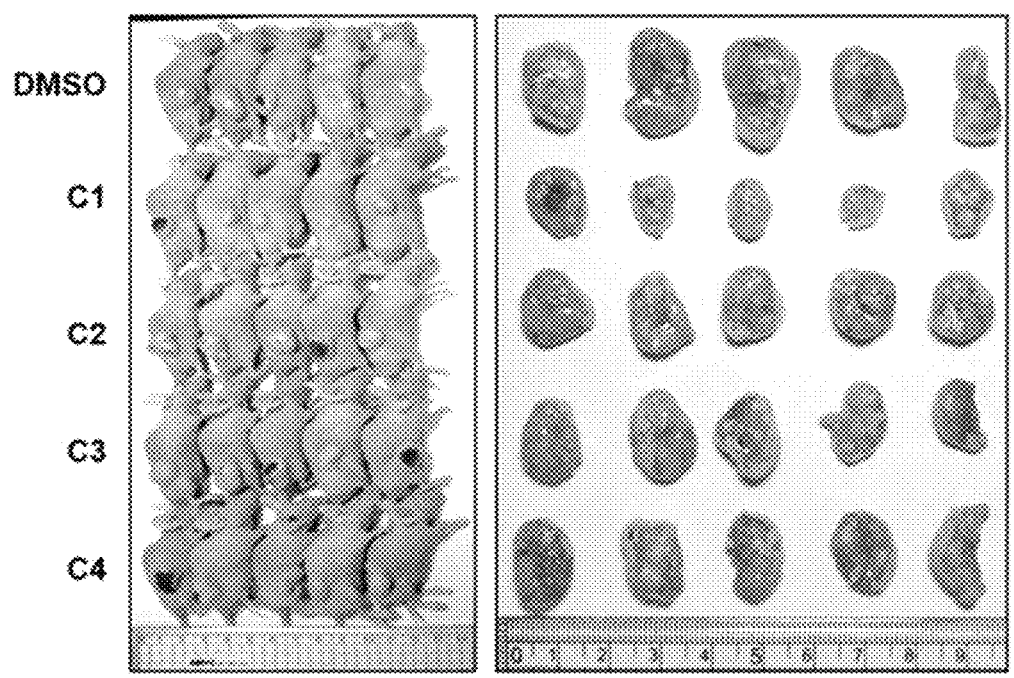
FIG. 23A shows images of MCF7/Dox xenograft tumors treated with DMSO control, C1, C2, C3, and C4. Tumors are shown (right).
Figure 23B:
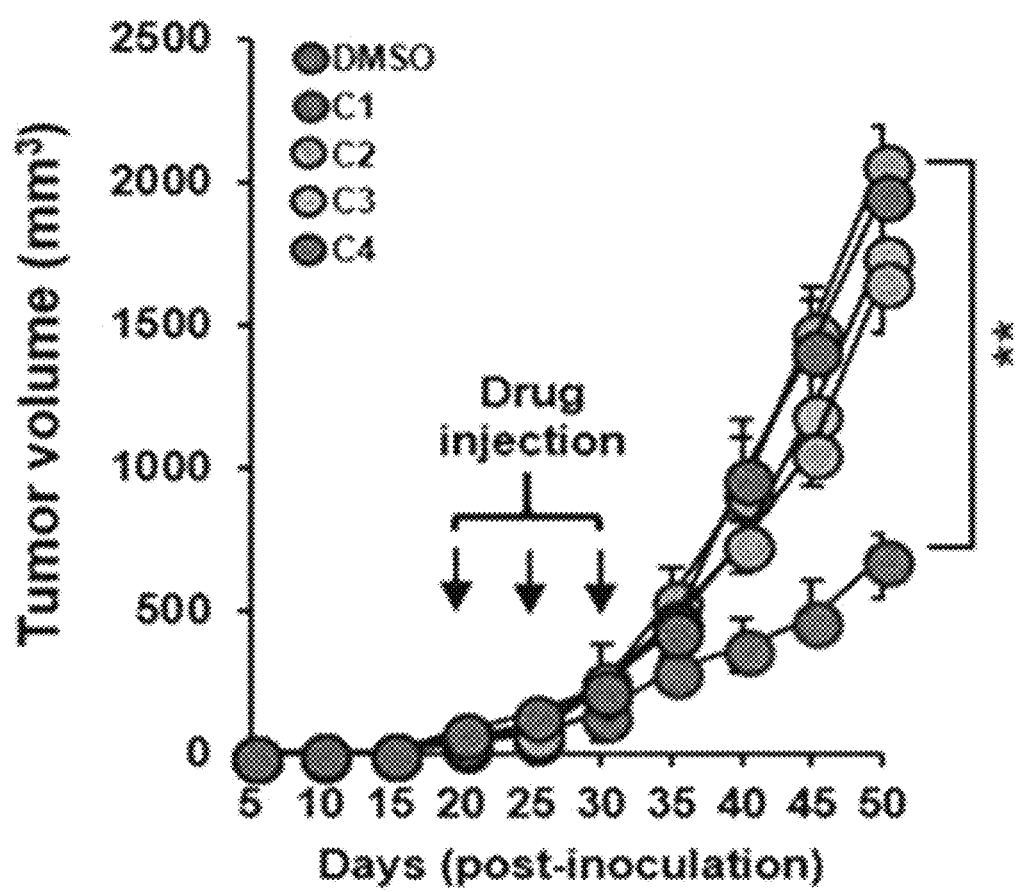
FIG. 23B shows tumor volumes of the mice in the DMSO control, C1, C2, C3, and C4 tumors (mean±SD, n=5 per group, , p<0.01).
Figure 23C:
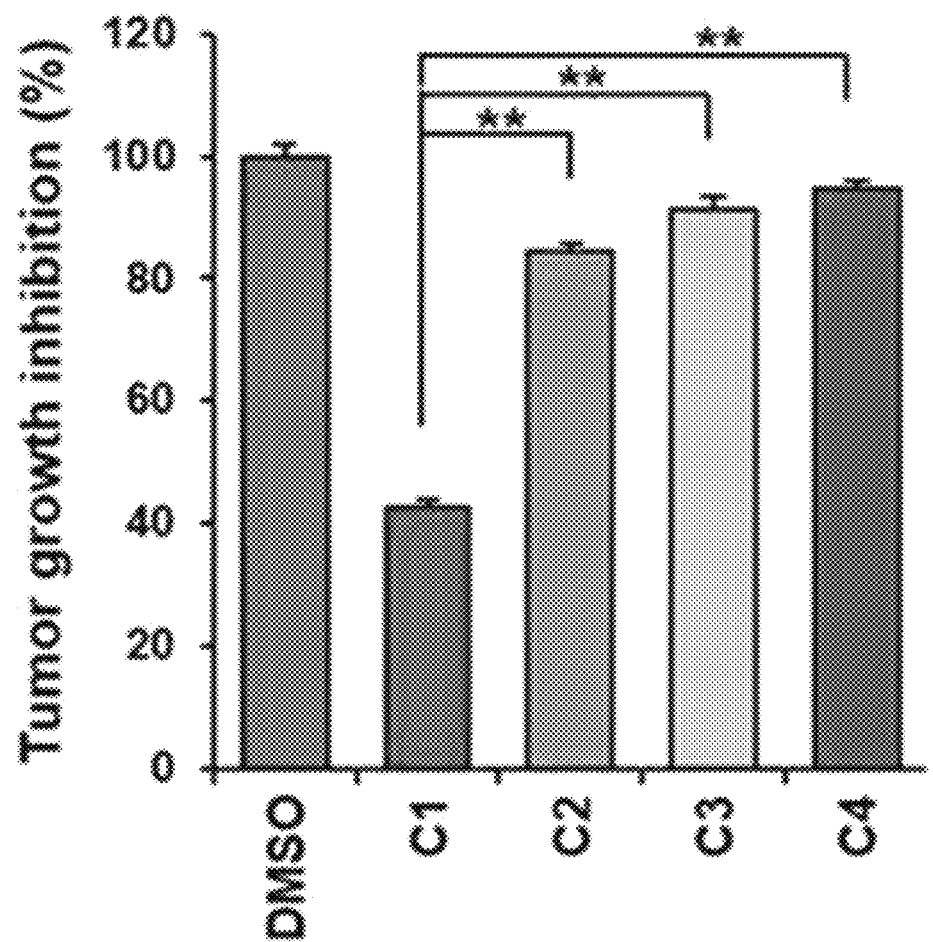
FIG. 23C shows tumor growth inhibition after treatment with DMSO (0.1%), or compounds (mean±SD, p<0.01). C1 injection led to a 58% reduction in tumor growth, which was statistically greater than the reductions seen in the case of C2 (16%), C3 (9%), C4 (6%) and DMSO (0%) tested under otherwise identical conditions.
Figure 23D:
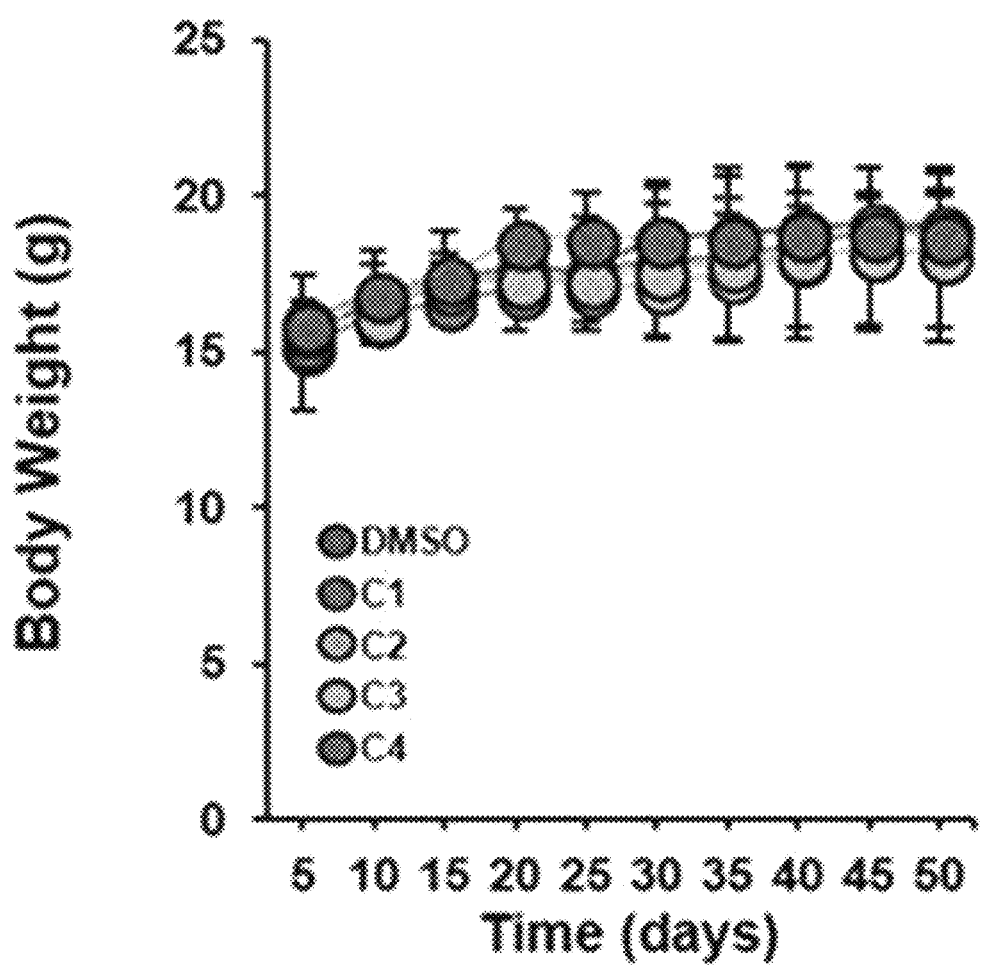
FIG. 23D shows body weight changes of nude mice bearing MCF7/Dox tumors observed upon treatment with DMSO, C1, C2, C3, and C4.
Figure 23E:
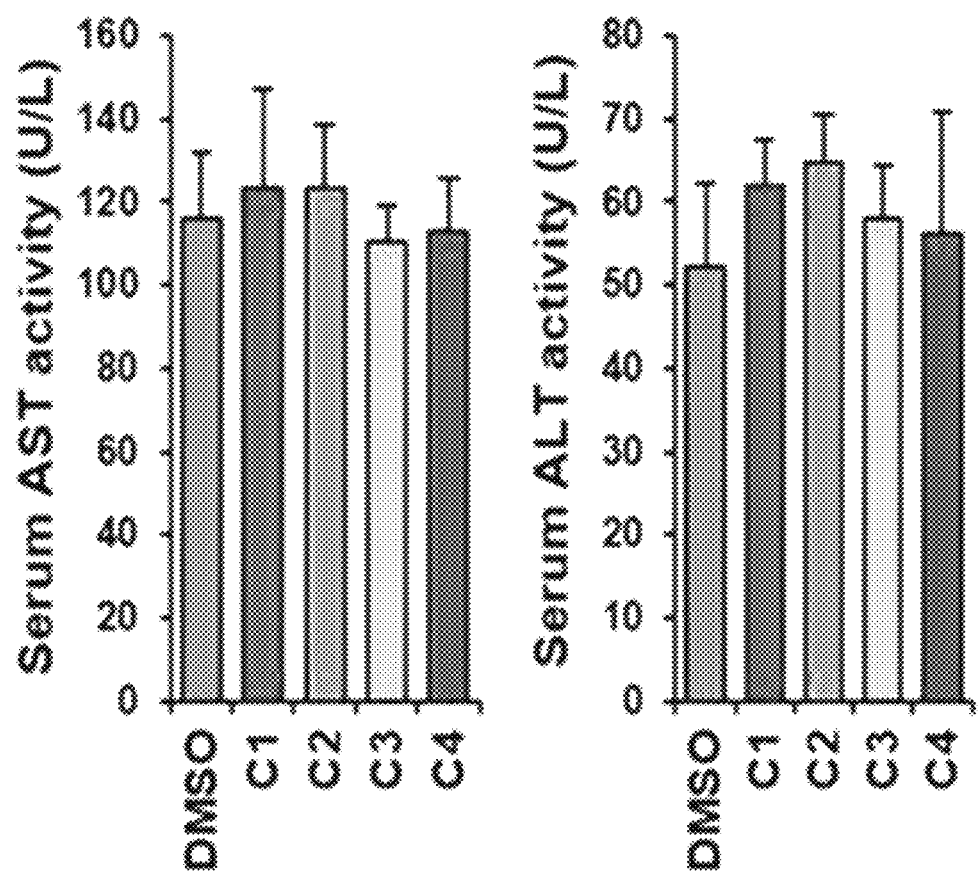
FIG. 23E shows AST and ALT activity levels for the mice in the DMSO control, C1, C2, C3 and C4 groups as determined from blood serum analyses (mean±SD, n=5 per group).

In light of the above results, an effort was made to test the potential of C1 to promote an in vivo therapeutic effect. Toward this end, conjugate C1 and formulations consisting of Dox+DCA (i.e., containing a mixture of Dox and DCA) were injected into mice bearing MCF and MCF7/Dox xenograft tumors (FIG. 21A). As can be seen from an inspection of FIG. 5D, conjugate C1 produced the greatest growth inhibition. Specifically, C1 injection led to reductions in the tumor volume of approximately 78% (MCF7) and 74% (MCF7/Dox), whereas the combined (Dox+DCA) treatment resulted in only a 53% and 18% reduction, respectively (FIG. 5E and FIG. 22B). The difference was statistically significant. Likewise, C1 induced a statistically greater level of tumor inhibition than C2-C4 when retested in an independent comparative study using the same MCF/Dox animal model (FIG. 23). No appreciable weight loss was observed for any groups over the course of treatment (FIG. 22C and FIG. 23D). Measurement of alanine aminotransferase (ALT) and aspartate aminotransferase (AST) levels in blood serum samples revealed no significant toxicity induced by either C1 or the control conjugates C2-C4 (FIG. 23E). Fluorescence image analysis of the mice and representative dissected organs revealed a highly tumor-specific accumulation of Dox in the case C1 (FIG. 5F). This finding is consistent with the suggestion that the inventive conjugate C1 overcomes efflux mechanisms associated with Dox-resistant tumor cells and can induce regression of drug-resistant tumors in vivo. The key finding is that the inventive conjugate C1 is active in promoting tumor growth inhibition for the resistant cell line xenograft (MCF7/Dox), whereas Dox+DCA and other tested controls C2-C4 are not appreciably effective.

What is claimed is:

1. An anticancer prodrug comprising a pyruvate dehydrogenase kinase (PDK) inhibitor moiety, a mitochondrial targeting group, and an anthracycline moiety reversibly connected to the PDK inhibitor moiety and the targeting group, wherein the PDK inhibitor moiety is represented by Structural Formula 1:

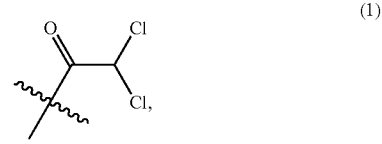 [SMILES: *C(=O)C(Cl)Cl]

wherein the mitochondrial targeting group is represented by Structural Formula 2:

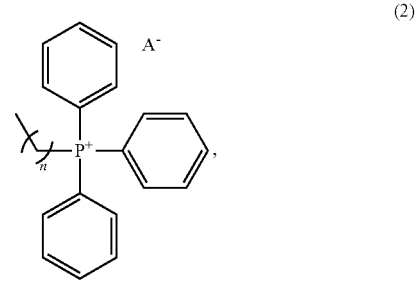

where A⁻ is halogen anion and n is an integer from 1 to 30, wherein the anthracycline is doxorubicin, and wherein the PDK inhibitor moiety, the mitochondrial targeting group, and the anthracycline moiety are connected to one another through a linker represented by Formula 3:

(3)

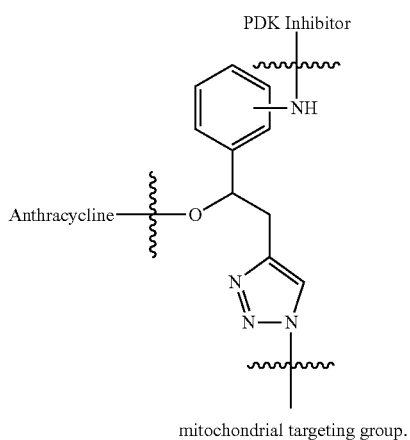

mitochondrial targeting group.

2. The anticancer prodrug according to claim 1, wherein the anticancer prodrug is activated by carboxylesterase to release the PDK inhibitor moiety and the anthracycline moiety.

3. The anticancer prodrug according to claim 2, wherein the released PDK inhibitor moiety shifts cancer cell metabolism from aerobic glycolysis (the Warburg effect) to oxidative phosphorylation (OXPHOS).

4. An anticancer prodrug represented by Formula 4:

(4)

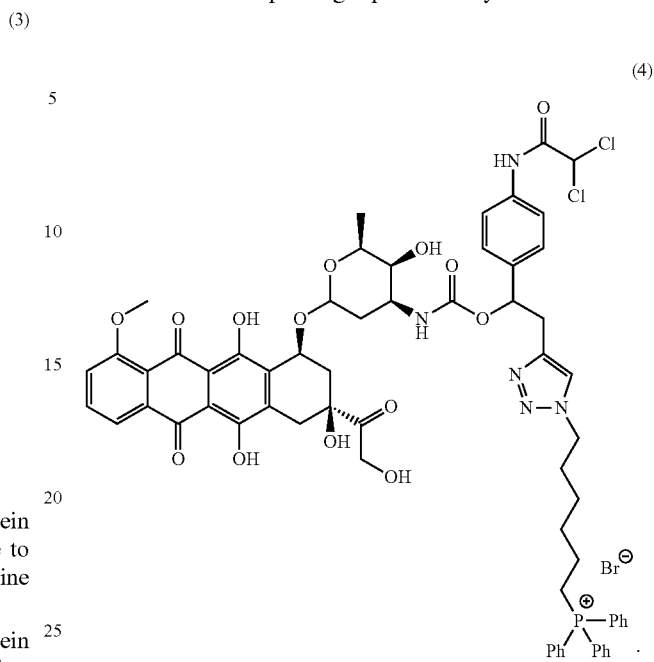

* * * * *